United States Patent
Katou

(10) Patent No.: US 12,173,188 B2
(45) Date of Patent: Dec. 24, 2024

(54) ULTRAVIOLET ABSORBING AGENT, ULTRAVIOLET ABSORBING COMPOSITION, ULTRAVIOLET ABSORBING FILM, LAMINATE, AND NOVEL COMPOUND

(71) Applicant: FUJIFILM CORPORATION, Tokyo (JP)

(72) Inventor: Takashi Katou, Shizuoka (JP)

(73) Assignee: FUJIFILM CORPORATION, Tokyo (JP)

( * ) Notice: Subject to any disclaimer, the term of this patent is extended or adjusted under 35 U.S.C. 154(b) by 586 days.

(21) Appl. No.: 17/522,943

(22) Filed: Nov. 10, 2021

(65) Prior Publication Data

US 2022/0064458 A1 Mar. 3, 2022

Related U.S. Application Data

(63) Continuation of application No. PCT/JP2020/021668, filed on Jun. 1, 2020.

(30) Foreign Application Priority Data

Jun. 28, 2019 (JP) .................. 2019-122032

(51) Int. Cl.
```
C09D 5/32       (2006.01)
C07D 339/06     (2006.01)
C07D 409/04     (2006.01)
C09D 7/63       (2018.01)
G02B 5/20       (2006.01)
C08K 5/45       (2006.01)
```

(52) U.S. Cl.
CPC .............. *C09D 5/32* (2013.01); *C07D 339/06* (2013.01); *C07D 409/04* (2013.01); *C09D 7/63* (2018.01); *G02B 5/208* (2013.01); *C08K 5/45* (2013.01)

(58) Field of Classification Search
CPC .......... C09D 5/32; C09D 7/63; C07D 339/06; C07D 409/04; C08K 5/45; G02B 5/208
See application file for complete search history.

(56) References Cited

U.S. PATENT DOCUMENTS

| | | | |
|---|---|---|---|
| 3,694,211 A | 9/1972 | Sato et al. | |
| 2010/0086849 A1 | 4/2010 | Mizuno et al. | |
| 2011/0076616 A1* | 3/2011 | Kubota | G03F 7/3035 430/281.1 |
| 2018/0319755 A1 | 11/2018 | Teng et al. | |

FOREIGN PATENT DOCUMENTS

| | | | | |
|---|---|---|---|---|
| CN | 101719542 A | 6/2010 | | |
| CN | 108349925 A | 7/2018 | | |
| JP | S49-11155 B1 | 3/1974 | | |
| JP | S60170842 A | * 9/1985 | ............... | C03C 1/40 |
| JP | 2009096984 A | * 5/2009 | ............ | C07D 249/20 |
| JP | 2009263617 A | * 11/2009 | ............ | C07D 409/04 |
| JP | 5364611 B2 | 12/2013 | | |
| JP | 2016-124817 A | 7/2016 | | |
| JP | 2017-088591 A | 5/2017 | | |
| WO | 2018/173979 A1 | 9/2018 | | |
| WO | 2019/065043 A1 | 4/2019 | | |
| WO | 2019/117082 A1 | 6/2019 | | |

OTHER PUBLICATIONS

English language translation of the following: Office action dated Nov. 1, 2023 from the SIPO in a Chinese patent application No. 202080042155.5 corresponding to the instant patent application. This office action translation is submitted now in order to supplement the understanding of the cited references which are being disclosed in the instant Information Disclosure Statement.
International Search Report issued in International Application No. PCT/JP2020/021668 on Aug. 18, 2020.
Written Opinion of the ISA issued in International Application No. PCT/JP2020/021668 on Aug. 18, 2020.
English language translation of the following: Office action dated Nov. 15, 2022 from the JPO in a Japanese patent application No. 2021-527542 corresponding to the instant patent application.
English language translation of the following: Office action dated May 10, 2024 from the SIPO in a Chinese patent application No. 202080042155.5 corresponding to the instant patent application.

\* cited by examiner

*Primary Examiner* — Bijan Ahvazi
(74) *Attorney, Agent, or Firm* — SOLARIS Intellectual Property Group, PLLC

(57) ABSTRACT

Provided are an ultraviolet absorbing agent represented by General Formula (1) and an application thereof. In General Formula (1), $R^{11}$ represents a monovalent substituent. n is 1 or 2. $W^1$ and $W^2$ each independently represent a hydrogen atom, a cyano group, a carbamoyl group, a sulfamoyl group, a nitro group, an acyl group, an alkylsulfonyl group, an arylsulfonyl group, an alkylsulfinyl group, an arylsulfinyl group, an alkoxycarbonyl group, an aryloxycarbonyl group, an alkyl group, an aryl group, or a heterocyclic group, where at least one of $W^1$ or $W^2$ represents a substituent having a Hammett's substituent constant σp value of 0.2 or more. $W^1$ and $W^2$ may be bonded to each other to form a ring.

(1)

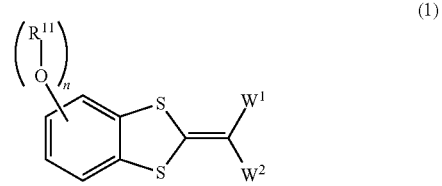

15 Claims, No Drawings

ULTRAVIOLET ABSORBING AGENT, ULTRAVIOLET ABSORBING COMPOSITION, ULTRAVIOLET ABSORBING FILM, LAMINATE, AND NOVEL COMPOUND

CROSS-REFERENCE TO RELATED APPLICATIONS

This application is a continuation application of International Application No. PCT/JP2020/021668, filed Jun. 1, 2020, the disclosure of which is incorporated herein by reference in its entirety. Further, this application claims priority from Japanese Patent Application No. 2019-122032, filed Jun. 28, 2019, the disclosure of which is incorporated herein by reference in its entirety.

BACKGROUND OF THE INVENTION

1. Field of the Invention

The present disclosure relates to an ultraviolet absorbing agent, an ultraviolet absorbing composition, an ultraviolet absorbing film, a laminate, and a novel compound.

2. Description of the Related Art

For the intended purpose of reducing the influence of ultraviolet rays, various inorganic ultraviolet absorbing agents, organic ultraviolet absorbing agents, and the like are used in combination with a liquid medium, a resin, or the like. Among them, organic ultraviolet absorbing agents are widely used as compared with inorganic ultraviolet absorbing agents due to the fact that they have a higher degree of freedom in prescription.

A large number of organic ultraviolet absorbing agents are oil-soluble compounds and are generally used by being blended with an organic solvent, an oil agent, or the like. In a case where an organic ultraviolet absorbing agent is used in combination with an aqueous medium, the ultraviolet absorbing agent may be dissolved in an oil component and blended as an oil in water type emulsified composition.

From the viewpoint of the burden on the environment, a water-soluble ultraviolet absorbing agent is required, and a water-soluble ultraviolet absorbing agent that absorbs a short-wavelength ultraviolet ray is known.

However, a water-soluble ultraviolet absorbing agent as the ultraviolet absorbing agent capable of absorbing a long-wavelength ultraviolet ray, which has a maximum absorption wavelength of 380 nm to 400 nm, has not been widely used.

Regarding the water-soluble ultraviolet absorbing agent, for example, a two-layer cosmetic material containing a phenylbenzimidazole compound having a sulfonic acid group as an ultraviolet absorbing agent has been proposed, and it is disclosed that the water-soluble ultraviolet absorbing agent blended in this cosmetic material has a solubility in water of 0.01% or more (see JP2016-124817A).

In addition, an ultraviolet absorbing agent having two benzodithiolane skeletons in the molecule and having an absorption maximum in a wavelength range of 360 nm or more has been proposed, and it is disclosed that the ultraviolet absorbing agent may contain a water-soluble group as a substituent (see JP5364611B).

Further, an ultraviolet absorbing agent having a benzodithiolane skeleton, which is capable of absorbing ultraviolet rays having a wavelength of 320 nm to 400 nm and in which a decrease in ultraviolet absorbing ability due to aging is suppressed, is disclosed, and it is described that the ultraviolet absorbing agent may have a carboxy group or a sulfo group as a water-soluble group (see JP2009-263617A).

SUMMARY OF THE INVENTION

According to the study of the inventors of the present invention, the ultraviolet absorbing agent described in JP2016-124817A has not achieved the degree of solubility in water, by which it can be stably present in an aqueous medium alone.

The ultraviolet absorbing agent described in J5364611B is good in the maintenance of ultraviolet absorbing ability. However, in a case where it is aged in a medium such as an aqueous medium or a water-soluble polymer, haze (turbidity) may occur by precipitation or aggregation due to crystallization, or haze may be increased, which leaves room for improvement in stability in the medium.

As the ultraviolet absorbing agent described in JP2009-263617A, a specific exemplary compound having a carboxy group as an acid group is disclosed; however, a compound in which a carboxy group is directly bonded to a benzene ring in a benzodithiolane skeleton is only disclosed. The disclosed compound has a problem of being inferior in stability in a medium, like the ultraviolet absorbing agent described in JP5364611B.

An object to be achieved by one aspect of the present invention is to provide an ultraviolet absorbing agent having an ultraviolet absorbing ability in a wavelength range of at least 380 nm to 400 nm, having good solubility in water, and having good aging-associated stability in an aqueous medium, and a water-soluble ultraviolet absorbing composition containing an aqueous medium and having good aging-associated stability.

An object to be achieved by another aspect of the present invention is to provide an ultraviolet absorbing film that has an ultraviolet absorbing ability in a wavelength range of at least 380 nm to 400 nm and contains a water-soluble polymer and in which an increase in the aging-associated haze is suppressed, and a laminate having the ultraviolet absorbing film.

In addition, an object to be achieved by another aspect of the present invention is to provide a novel compound having an ultraviolet absorbing ability in a wavelength range of at least 380 nm to 400 nm.

The means for achieving the above objects includes the following aspects.

<1> An ultraviolet absorbing agent represented by General Formula (1).

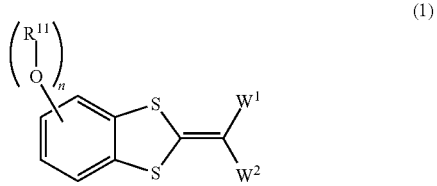

(1)

In General Formula (1), $R^{11}$ represents a monovalent substituent, n is 1 or 2, where in a case where n is 2, two existing $R^{11}$'s may be the same or different from each other, $W^1$ and $W^2$ each independently represent a hydrogen atom, a cyano group, a carbamoyl group, a sulfamoyl group, a nitro group, an acyl group, an alkylsulfonyl group, an arylsulfonyl group, an alkylsulfinyl group, an arylsulfinyl group, an alkoxycarbonyl group, an aryloxycarbonyl group, an alkyl group, an aryl group, or a heterocyclic group, where at least one of $W^1$ or $W^2$ represents a substituent having a Hammett's substituent constant σp value of 0.2 or more, and $W^1$ and $W^2$ may be bonded to each other to form a ring, and at least one group of $R^{11}$, $W^1$, or $W^2$ has an acid group selected from the group consisting of a sulfonic acid group, a carboxylic acid group, and a phosphoric acid group.

<2> The ultraviolet absorbing agent according to <1>, in which the ultraviolet absorbing agent is represented by General Formula (2).

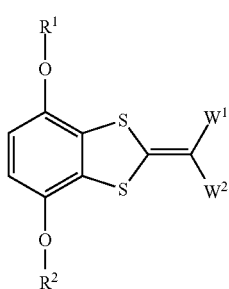

(2)

In General Formula (2), $R^1$ and $R^2$ each independently represent a monovalent substituent, $W^1$ and $W^2$ each independently represent a hydrogen atom, a cyano group, a carbamoyl group, a sulfamoyl group, a nitro group, an acyl group, an alkylsulfonyl group, an arylsulfonyl group, an alkylsulfinyl group, an arylsulfinyl group, an alkoxycarbonyl group, an aryloxycarbonyl group, an alkyl group, an aryl group, or a heterocyclic group, where at least one of $W^1$ or $W^2$ represents a substituent having a Hammett's substituent constant σp value of 0.2 or more, and $W^1$ and $W^2$ may be bonded to each other to form a ring, and at least one group of $R^1$, $R^2$, $W^1$, or $W^2$ has an acid group selected from the group consisting of a sulfonic acid group, a carboxylic acid group, and a phosphoric acid group.

<3> The ultraviolet absorbing agent according to <1>, in which the ultraviolet absorbing agent is represented by General Formula (3).

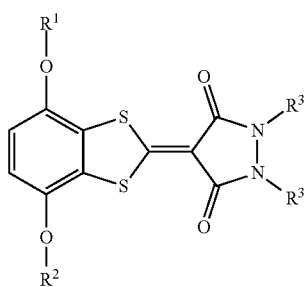

(3)

In General Formula (3), $R^1$ and $R^2$ each independently represent a monovalent substituent, $R^3$ represents an alkyl group, an aryl group, or a heterocyclic group, and at least one group of $R^1$, $R^2$, or $R^3$ has an acid group selected from the group consisting of a sulfonic acid group, a carboxylic acid group, and a phosphoric acid group.

<4> The ultraviolet absorbing agent according to any one of <1> to <3>, in which the acid group is a sulfonic acid group.

<5> The ultraviolet absorbing agent according to any one of <1> to <4>, in which a solubility in water at 25° C. is 1% by mass or more.

<6> An ultraviolet absorbing composition comprising the ultraviolet absorbing agent according to any one of <1> to <5> and an aqueous medium.

<7> The ultraviolet absorbing composition according to <6>, further comprising a water-soluble polymer.

<8> An ultraviolet absorbing film, in which the ultraviolet absorbing film is a cured substance of the ultraviolet absorbing composition according to <6> or <7>.

<9> A laminate comprising a base material and the ultraviolet absorbing film according to <8>, formed on the base material.

<10> A compound represented by General Formula (4).

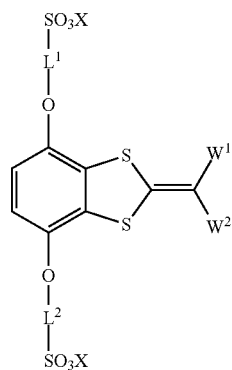

(4)

In General Formula (4), $L^1$ and $L^2$ each independently represent an alkylene group, X's each independently represent a hydrogen atom or a countercation of $-SO_3^-$, $W^1$ and $W^2$ each independently represent a hydrogen atom, a cyano group, a carbamoyl group, a sulfamoyl group, a nitro group, an acyl group, an alkylsulfonyl group, an arylsulfonyl group, an alkylsulfinyl group, an arylsulfinyl group, an alkoxycarbonyl group, an aryloxycarbonyl group, an alkyl group, an aryl group, or a heterocyclic group, where at least one of W' or $W^2$ represents a substituent having a Hammett's substituent constant σp value of 0.2 or more, and $W^1$ and $W^2$ may be bonded to each other to form a ring.

According to one aspect of the present invention, it is possible to provide an ultraviolet absorbing agent having an ultraviolet absorbing ability in a wavelength range of at least 380 nm to 400 nm, having good solubility in water, and having good aging-associated stability in an aqueous medium, and a water-soluble ultraviolet absorbing composition containing an aqueous medium and having good aging-associated stability.

According to another aspect of the present invention, it is possible to provide an ultraviolet absorbing film that has an ultraviolet absorbing ability in a wavelength range of at least 380 nm to 400 nm and contains a water-soluble polymer and in which an increase in the aging-associated haze is suppressed, and a laminate having the ultraviolet absorbing film.

In addition, according to another aspect of the present invention, a novel compound having an ultraviolet absorbing ability in a wavelength range of at least 380 nm to 400 nm is provided.

DESCRIPTION OF THE PREFERRED EMBODIMENTS

Hereinafter, an ultraviolet absorbing agent, an ultraviolet absorbing composition, an ultraviolet absorbing film, a laminate, and a compound of the present disclosure will be described.

However, the ultraviolet absorbing agent, the ultraviolet absorbing composition, the laminate, and the novel compound of the present disclosure are not limited to the embodiments described below, and can be embodied by being appropriately modified within the scope of the object of the present disclosure.

A range of numerical values indicated using "to" in the present disclosure means a range including numerical values before and after "to" as a minimum value and a maximum value.

In the range of numerical values described stepwise in the present disclosure, an upper limit value and a lower limit value, described in a certain range of numerical values, may be replaced with an upper limit value and a lower limit value, described in another range of numerical values described in stepwise. In addition, in the range of numerical values described in the present disclosure, an upper limit value and a lower limit value, described in a certain range of numerical values, may be replaced with values shown in examples.

In addition, in the present disclosure, a combination of two or more preferred aspects is a more preferred aspect.

In the present disclosure, in a case where plural kinds of substances corresponding to each component are present, the content of each component means a content of all of the plural kinds of substances, unless otherwise noted.

In the present disclosure, (meth)acryl means at least one of acryl or methacryl, and (meth)acrylate means at least one of acrylate or methacrylate.

Unless otherwise specified, the term "substituent" is used in the meaning in which an unsubstituted group and a group having an additional substituent are included. For example, in a case where the term "alkyl group" is used, it is used in the meaning in which both an unsubstituted alkyl group and an alkyl group having an additional substituent are included. The same applies to other substituents.

In the present disclosure, the term "step" includes not only an independent step but also a step that cannot be clearly distinguished from other steps, as long as the intended purpose of the step is achieved.

In the present disclosure, "a compound is water-soluble" means that 1% by mass or more of a compound is dissolved in water at 25° C.

In addition, the "ultraviolet absorbing ability" in the present disclosure means that ultraviolet rays in a wavelength range of at least 380 nm to 400 nm are absorbed and includes not only a case where ultraviolet rays in a wavelength range of 380 nm to 400 nm are completely blocked by absorption but also a case where at least a part of the ultraviolet rays are absorbed and the transmittance of the ultraviolet rays are reduced.

[Ultraviolet absorbing agent represented by General Formula (1)]

The ultraviolet absorbing agent of the present disclosure is represented by General Formula (1).

Hereinafter, the ultraviolet absorbing agent represented by General Formula (1) may be referred to as a "specific ultraviolet absorbing agent".

[Specific Ultraviolet Absorbing Agent]

The specific ultraviolet absorbing agent of the present disclosure is represented by General Formula (1).

The specific ultraviolet absorbing agent is a compound having only one benzodithiolane skeleton in the molecule and preferably has a maximum absorption wavelength in a wavelength range of 380 nm to 400 nm.

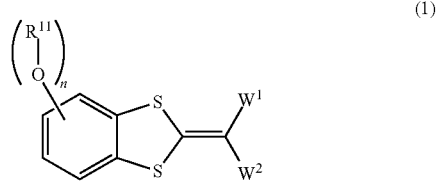

(1)

In General Formula (1), $R^{11}$ represents a monovalent substituent, n is 1 or 2, where in a case where n is 2, two existing $R^{11}$'s may be the same or different from each other, and $W^2$ each independently represent a hydrogen atom, a cyano group, a carbamoyl group, a sulfamoyl group, a nitro group, an acyl group, an alkylsulfonyl group, an arylsulfonyl group, an alkylsulfinyl group, an arylsulfinyl group, an alkoxycarbonyl group, an aryloxycarbonyl group, an alkyl group, an aryl group, or a heterocyclic group, where at least one of $W^1$ or $W^2$ represents a substituent having a Hammett's substituent constant σp value of 0.2 or more. $W^1$ and $W^2$ may be bonded to each other to form a ring.

At least one group of $R^{11}$, $W^1$, or $W^2$ has an acid group selected from the group consisting of a sulfonic acid group, a carboxylic acid group, and a phosphoric acid group.

The action mechanism of the present disclosure is not clear; however, it is presumed as follows.

It is presumed that the specific ultraviolet absorbing agent of the present disclosure has only one benzodithiolane skeleton in the molecule, and thus the crystallization rate becomes slow. Further, the acid group in the specific ultraviolet absorbing agent has a structure that is bonded to the benzene ring or the dithiolane skeleton through an oxygen atom, and thus it is conceived that the precipitation caused by crystallization is suppressed for a long period of time and the stability in an aqueous medium is improved, for example, even in a case where the specific ultraviolet absorbing agent is allowed to be aged in an aqueous medium.

Due to the slow crystallization rate of the specific ultraviolet absorbing agent, it is presumed that the precipitation, the aggregation, and the like of the specific ultraviolet absorbing agent, which are caused by crystallization, are suppressed and the increase in the haze of the ultraviolet absorbing film is suppressed over a long period of time, even in the ultraviolet absorbing film as a cured substance of the ultraviolet absorbing composition containing the specific ultraviolet absorbing agent.

In addition, the specific ultraviolet absorbing agent has a good ultraviolet absorbing ability in a wavelength range of at least 380 nm to 400 nm due to the benzodithiolane skeleton contained in the molecule.

Since the maximum absorption wavelength of the specific ultraviolet absorbing agent is larger than 380 nm, a better ultraviolet blocking property is obtained on the long wavelength side, and since it is smaller than 400 nm, the coloring in a cured substance of the ultraviolet absorbing composition containing the specific ultraviolet absorbing agent, for example, the ultraviolet absorbing film is suppressed.

The action mechanism described above is a presumable one and does not impose any restrictions on the present disclosure.

The maximum absorption wavelength of the ultraviolet absorbing agent can be measured, for example, using a spectrophotometer. Examples of the device include a spectrophotometer UV3600 and an ultraviolet-visible-near infrared spectrophotometer UV 3150, manufactured by Shimadzu Corporation. In the present disclosure, the maximum absorption wavelength of the ultraviolet absorbing agent is measured using a spectrophotometer UV3600.

The measurement is carried out at room temperature (25° C.), and the absorbance is measured using a spectrophotometer to obtain an absorption spectrum while air is referenced as a control as the measurement condition.

In a case where an absorbance at a wavelength in a predetermined wavelength range is measured, the maximum absorption wavelength, the transmittance, and the like can be calculated.

Each substituent in General Formula (1) will be described.

In General Formula (1), $R^{11}$ represents a monovalent substituent, Examples of the monovalent substituent include an alkyl group, an aryl group, a heterocyclic group, an acyl group, a carbamoyl group, an alkoxycarbonyl group, an aryloxycarbonyl group, an alkylsulfonyl group, an arylsulfonyl group, and a sulfamoyl group. The monovalent substituent is preferably an alkyl group, an aryl group, an alkoxycarbonyl group, or the like, from the viewpoint that the crystallization rate of the specific ultraviolet absorbing agent can be suppressed to a lower level.

The monovalent substituent may be unsubstituted or may have an additional substituent.

In a case where the monovalent substituent as $R^{11}$ has an additional substituent, Examples of the substituent introduceable thereto include a group selected from the group consisting of the substituents exemplified as the above monovalent substituent, and an acid group selected from the group consisting of a sulfonic acid group, a carboxylic acid group, and a phosphoric acid group.

The alkyl group as the monovalent substituent may be linear, may have a branch, or may form a ring. The alkyl group preferably has 1 to 20 carbon atoms and more preferably 1 to 18 carbon atoms.

Examples of the alkyl group include a methyl group, an ethyl group, an n-propyl group, an isopropyl group, a t-butyl group, an n-octyl group, an eicosyl group, a 2-chloroethyl group, a 2-cyanoethyl group, a 2-ethylhexyl group, a cyclohexyl group, a cyclopentyl group, and a 4-n-dodecylcyclohexyl group.

The aryl group is preferably an aryl group having 6 to 30 carbon atoms, and examples thereof include a phenyl group, a p-tolyl group, a naphthyl group, an m-chlorophenyl group, and an o-hexadecanoylaminophenyl group, and a phenyl group is preferable.

The heterocyclic group is a monovalent group obtained by removing one hydrogen atom from an aromatic or non-aromatic heterocyclic compound, and the heterocyclic groups may be further fused.

The heterocyclic group is preferably a 5-membered or 6-membered heterocyclic group, and the heteroatom that constitutes the ring is preferably an oxygen atom, a sulfur atom, or a nitrogen atom. It is more preferably a 5-membered or 6-membered aromatic heterocyclic group having 3 to 30 carbon atoms.

Examples of the heterocyclic ring in the heterocyclic group include a pyridine ring, a pyrazine ring, a pyridazine ring, a pyrimidine ring, a triazine ring, a quinoline ring, an isoquinoline ring, a quinazoline ring, a cinnoline ring, a phthalazine ring, a quinoxaline ring, a pyrrole ring, an indole ring, a furan ring, a benzofuran ring, a thiophene ring, a benzothiophene ring, a pyrazole ring, an imidazole ring, a benzimidazole ring, a triazole ring, an oxazole ring, a benzoxazole ring, a thiazole ring, a benzothiazole ring, an isothiazole ring, a benzisothiazole ring, a thiadiazole ring, an isooxazole ring, a benzisooxazole ring, a pyrrolidine ring, a piperidine ring, a piperazine ring, a imidazolidine ring, and a thiazoline ring.

The acyl group is preferably a formyl group, an aliphatic carbonyl group having 2 to 30 carbon atoms (for example, an alkylcarbonyl group), an arylcarbonyl group having 7 to 30 carbon atoms (preferably a phenylcarbonyl group), or a heterocyclic carbonyl group bonded to a carbonyl group with 4 to 30 carbon atoms.

Examples of the acyl group include an acetyl group, a pivaloyl group, a 2-chloroacetyl group, a stearoyl group, a benzoyl group, a p-n-octyloxyphenylcarbonyl group, a 2-pyridylcarbonyl group, and a 2-furylcarbonyl group.

The carbamoyl group is preferably a carbamoyl group having 1 to 30 carbon atoms. Examples of the carbamoyl group include a carbamoyl group, an N-methylcarbamoyl group, an N,N-dimethylcarbamoyl group, an N,N-di-n-octylcarbamoyl group, and an N-(methyl sulfonyl)carbamoyl group.

The alkoxycarbonyl group is preferably an alkoxycarbonyl group having 2 to 20 carbon atoms and more preferably an alkoxycarbonyl group having 2 to 9 carbon atoms.

Examples of the alkoxycarbonyl group include a methoxycarbonyl group, an ethoxycarbonyl group, a t-butoxycarbonyl group, and a benzyloxycarbonyl group.

The aryloxycarbonyl group is preferably an aryloxycarbonyl group having 7 to 30 carbon atoms. Examples of the aryloxycarbonyl group include a phenoxycarbonyl group, an o-chlorophenoxycarbonyl group, an m-nitrophenoxycarbonyl group, and a p-tert-butylphenoxycarbonyl group. It is preferably a phenyloxycarbonyl group.

Examples of the alkylsulfonyl group or the arylsulfonyl group include an aliphatic sulfonyl group having 1 to 30 carbon atoms (for example, an alkylsulfonyl group) and an arylsulfonyl group having 6 to 30 carbon atoms (preferably a phenylsulfonyl group). Specific examples thereof include a methylsulfonyl group, an ethylsulfonyl group, a phenylsulfonyl group, and a p-toluenesulfonyl group.

The sulfamoyl group is preferably a sulfamoyl group having 0 to 30 carbon atoms. Examples of the sulfamoyl group include a sulfamoyl group, an N,N-dimethylaminosulfonyl group, and an N-n-octylaminosulfonyl group.

In General Formula (1), n is 1 or 2, and n is preferably 2 from the viewpoint that the solubility in water and the stability in an aqueous medium is better in the specific ultraviolet absorbing agent. In a case where n is 2, two existing $R^{11}$'s may be the same or different from each other. From the viewpoint of synthetic suitability, it is preferable that they are the same.

$W^1$ and $W^2$ each independently represent a hydrogen atom, a cyano group, an alkyloxycarbonyl group, an arylcarbonyl group, a carbamoyl group, a sulfamoyl group, a nitro group, an acyl group, an alkylsulfonyl group, an arylsulfonyl group, an alkylsulfinyl group, an arylsulfinyl group, an alkoxycarbonyl group, an aryloxycarbonyl group, an alkyl group, an aryl group, or a heterocyclic group, where at least one of $W^1$ or $W^2$ represents a substituent having a Hammett's substituent constant σp value of 0.2 or more.

$W^1$ and $W^2$ may have an additional substituent as long as they can be introduced thereto.

The Hammettt's substituent constant σp value will be described.

The Hammettt's rule is a rule of thumb proposed by L. P. Hammettt in 1935 for quantitatively discussing the effect of a substituent on the reaction or equilibrium of a benzene derivative, the validity of which is widely accepted today. The substituent constant obtained by the Hammettt's rule includes a σp value and a σm value, and these values can be found in many general books in the related field. For example, "Lange's Handbook of Chemistry" edited by J. A. Dean, 12th Edition, 1979 (McGraw-Hill), "Journal of Japanese Chemistry" Special Edition, No. 122, pp. 96 to 103, 1979 (Nankodo Co., Ltd.), and Chem. Rev., 1991, Volume 91, pp. 165 to 195 are mentioned.

In the present disclosure, a substituent having a Hammett's substituent constant σp of 0.2 or more indicates that it is an electron-withdrawing group. The σp value is preferably 0.25 or more, more preferably 0.3 or more, and particularly preferably 0.35 or more. The upper limit of the σp value is not particularly limited; however, it is preferably 1.20 or less and more preferably 1.00 or less.

Examples of the substituent having a Hammett's substituent constant σp value of 0.2 or more include a cyano group (0.66), an alkoxycarbonyl group (—COOMe: 0.45), an aryloxycarbonyl group (—COOPh: 0.44), a carbamoyl group (—CONH$_2$: 0.36), an alkylcarbonyl group (—COMe: 0.50), an arylcarbonyl group (—COPh: 0.43), and an alkylsulfonyl group (—SO$_2$Me: 0.72). In addition, the σp value of the carboxylic acid group (—COOH) which may be contained in $W^1$ or $W^2$ as an acid group is 0.45, and such a group is included in the substituent having a σp value of 0.2 or more.

In the present disclosure, a methyl group may be abbreviated as Me, and a phenyl group may be abbreviated as Ph.

The values in parentheses are σp values of the representative substituents selected from Chem. Rev., 1991, Volume 91, pp. 165 to 195.

Examples of the carbamoyl group, the sulfamoyl group, the nitro group, the acyl group, the alkylsulfonyl group, the arylsulfonyl group, the alkylsulfinyl group, the arylsulfinyl group, the alkoxycarbonyl group, the aryloxycarbonyl group, the alkyl group, and the aryl group, as $W^1$ and $W^2$, are the same as those exemplified as $R^{11}$.

In a case where $W^1$ and $W^2$ represent a heterocyclic group, the heterocyclic group is preferably a heterocyclic group obtained by removing one hydrogen atom from a 5-membered or 6-membered, saturated or unsaturated heterocyclic ring. The heterocyclic ring may be further fused with an aliphatic ring, an aromatic ring, or another heterocyclic ring.

Examples of the heteroatom contained in the heterocyclic ring include B, N, O, S, Se, and Te. The heteroatom is preferably N, O, or S.

In the heterocyclic ring, carbon atoms have a free valency (a monovalency), and a carbon atom in the heterocyclic group is bonded to an adjacent carbon atom, oxygen atom, or nitrogen atom.

The heterocyclic group may have an additional substituent, and examples of the substituent introducible thereto include the substituents described in paragraphs [0020] to [0039] of JP2008-81445A.

The heterocyclic group preferably has 3 to 40 carbon atoms, more preferably 3 to 30, and still more preferably 3 to 20 carbon atoms. Examples of the saturated heterocyclic ring include a pyrrolidine ring, a morpholine ring, a 2-bora-1,3-dioxolane ring, and a 1,3-thiazolidine ring. Examples of the unsaturated heterocyclic ring include an imidazole ring, a thiazole ring, a benzothiazole ring, a benzoxazole ring, a benzotriazole ring, a benzoselenazole ring, a pyridine ring, a pyrimidine ring, and a quinoline ring, and a heterocyclic group obtained by removing one hydrogen atom from these saturated heterocyclic rings is preferable.

$W^1$ and $W^2$ may be bonded to each other to form a ring, and examples of the ring that can be formed by $W^1$ and $W^2$ include an aliphatic ring, an aromatic ring, and a heterocyclic ring. The ring may be a fused ring obtained fusing two or more rings. Specific examples of the ring that can be formed by $W^1$ and $W^2$ include cyclohexane-1,3-dione, cyclopentane-1,3-dione, and pyrazolidine-1,3-dione.

In General Formula (1), at least one group of $R^u$, $W^1$, or $W^2$ has an acid group selected from the group consisting of a sulfonic acid group, a carboxylic acid group, and a phosphoric acid group. An acid group is located at any position, and an acid group may be bonded to the substituent exemplified as the substituent of $R^u$, $W^1$, and $W^2$.

In a case where at least one group of $R^u$, $W^1$, or $W^2$ has an acid group, any number of acid groups is contained in each group; however, an aspect in which each group has one acid group is preferable from the viewpoint of synthetic suitability.

The acid group is preferably a sulfonic acid group or a phosphoric acid group and more preferably a sulfonic acid group from the viewpoint that the solubility of the specific ultraviolet absorbing agent in water is better.

The acid group may be in a salt state. Examples of the salt of the acid group, which can be dissociated to be a countercation in an aqueous medium, include an alkali metal salt such as a sodium salt, a potassium salt, or a lithium salt, and a quaternary ammonium salt.

The number of acid groups in the compound represented by General Formula (1) may be 1 or more, and the compound may have 2 or more acid groups. The upper limit of the number of acid groups is not particularly limited; however, it is preferably 5 or less. The number of acid groups contained in the specific ultraviolet absorbing agent is preferably 1 to 4 and preferably 2 to 3 from the viewpoint that the solubility in water and the stability in an aqueous medium is better in the specific ultraviolet absorbing agent.

In a case where the specific ultraviolet absorbing agent has two or more acid groups, a plurality of acid groups may be the same or different from each other. For synthetic suitability, it is preferable that the plurality of acid groups are the same as each other.

The specific ultraviolet absorbing agent preferably has a solubility in water at 25° C. of 1% by mass from the viewpoint of stability in an aqueous medium. The solubility in water at 25° C. is more preferably 1.5% by mass or more, still more preferably 2% by mass or more, and even still more preferably 3% by mass or more.

The solubility of the specific ultraviolet absorbing agent in water in the present disclosure can be measured by the following method from the amount of the specific ultraviolet absorbing agent dissolved in 10 g of distilled water at 25° C.

After mixing 10 g of distilled water with 1 g of the specific ultraviolet absorbing agent, the resultant mixture is irradiated with ultrasonic waves at a liquid temperature of 25° C. for 15 minutes and then allowed to stand for 24 hours while the liquid temperature is maintained at 25° C. For ultrasonic irradiation, a desktop ultrasonic cleaner 1510, manufactured by Branson Ultrasonics, Emerson Japan, Ltd. is used.

After being allowed to stand for 24 hours, filtration is carried out through a membrane filter (0.1 μm mesh, manufactured by ADVANTEC Co., Ltd.). The unfiltered specific ultraviolet absorbing agent is collected, dried, and then weighed. The amount of the unfiltered specific ultraviolet absorbing agent is subtracted from 1 g of the specific ultraviolet absorbing agent to obtain an amount of the specific ultraviolet absorbing agent dissolved in water, and the solubility of the specific ultraviolet absorbing agent in water is calculated from that the obtained amount value.

Examples of the preferred aspect of the compound represented by General Formula (1) include a compound represented by General Formula (2). The ultraviolet absorbing agent represented by General Formula (1) is preferably an ultraviolet absorbing agent represented by General Formula (2) from the viewpoint that ultraviolet rays having a longer wavelength are efficiently absorbed and the viewpoint that the solubility in water is higher.

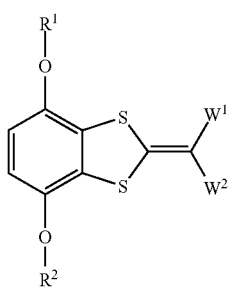

(2)

In General Formula (2), $R^1$ and $R^2$ each independently represent a monovalent substituent, $W^1$ and $W^2$ each independently represent a hydrogen atom, a cyano group, a carbamoyl group, a sulfamoyl group, a nitro group, an acyl group, an alkylsulfonyl group, an arylsulfonyl group, an alkylsulfinyl group, an arylsulfinyl group, an alkoxycarbonyl group, an aryloxycarbonyl group, an alkyl group, an aryl group, or a heterocyclic group, where at least one of $W^1$ or $W^2$ represents a substituent having a Hammett's substituent constant σp value of 0.2 or more. $W^1$ and $W^2$ may be bonded to each other to form a ring.

At least one group of $R^1$, $R^2$, or $W^2$ has an acid group selected from the group consisting of a sulfonic acid group, a carboxylic acid group, and a phosphoric acid group.

In General Formula (2), $R^1$ and $R^2$ are each synonymous with $R^{11}$ in General Formula (1) described above, and the same applies to the preferred examples thereof.

In General Formula (2), $W^1$ and $W^2$ are each independently synonymous with $W^1$ and $W^2$ in General Formula (1) described above.

In General Formula (2), $W^1$ and $W^2$ are preferably a cyano group, an alkylcarbonyl group, an arylcarbonyl group, an alkylsulfonyl group, an arylsulfonyl group, an alkylsulfinyl group, an arylsulfinyl group, an alkoxycarbonyl group, an aryloxycarbonyl group, or the like, and more preferably a cyano group, an alkylcarbonyl group, an arylcarbonyl group, an alkoxycarbonyl group, or the like, from the viewpoint that the solubility in water and the stability in an aqueous medium is better in the specific ultraviolet absorbing agent.

In General Formula (2), the acid group contained in at least one group of $R^1$, $R^2$, $W^1$, or $W^2$ is selected from the group consisting of a sulfonic acid group, a carboxylic acid group, and a phosphoric acid group, and it is preferably a sulfonic acid group or a phosphoric acid group and more preferably a sulfonic acid group. The acid group may be in a salt state as described above.

The number of acid groups in the compound represented by General Formula (2) may be 1 or more, and the compound may have 2 or more acid groups. The upper limit of the number of acid groups is the same as the case of General Formula (1).

The number of acid groups in General Formula (2) is preferably 1 to 3 and more preferably 2 from the viewpoint that the solubility in water and the stability in an aqueous medium is better in the specific ultraviolet absorbing agent.

In a case where the specific ultraviolet absorbing agent represented by General Formula (2) has two or more acid groups, a plurality of acid groups may be the same or different from each other. For synthetic suitability, it is preferable that the plurality of acid groups are the same as each other.

Examples of the preferred combination of the substituents in General Formula (2) include a combination in which $R^1$ and $R^2$ are an alkyl group having a sulfonic acid group, a phosphoric acid group, or a carboxylic acid group, and one of $W^1$ and $W^2$ is a cyano group and the other is an arylcarbonyl group or an alkylcarbonyl group, a combination in which $R^1$ and $R^2$ are an alkyl group having a sulfonic acid group and both $W^1$ and $W^2$ are a cyano group, a combination in which $R^1$ and $R^2$ are an alkyl group having a sulfonic acid group, and one of $W^1$ and $W^2$ are a cyano group and the other is alkoxyimino group, and a combination in which $R^1$ and $R^2$ are an alkyl group having a sulfonic acid group, and one of $W^1$ and $W^2$ are a cyano group and the other is a sulfoalkyl group.

Other examples of the preferred aspect of the compound represented by General Formula (1) include a compound represented by General Formula (3). The ultraviolet absorbing agent represented by General Formula (1) is preferably an ultraviolet absorbing agent represented by General Formula (3) from the viewpoint that the light stability is higher and the viewpoint that the solubility in water is higher.

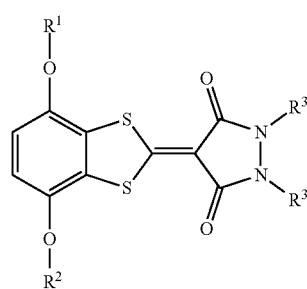

(3)

In General Formula (3), $R^1$ and $R^2$ each independently represent a monovalent substituent, $R^3$ represents an alkyl group, an aryl group, or a heterocyclic group, and at least one group of $R^1$, $R^2$, or $R^3$ has an acid group selected from the group consisting of a sulfonic acid group, a carboxylic acid group, and a phosphoric acid group.

In General Formula (3), $R^1$ and $R^2$ are each synonymous with $R^{11}$ in General Formula (1) described above, and the same applies to the preferred examples thereof.

In General Formula (3), $R^3$ represents an alkyl group, an aryl group, or a heterocyclic group, and it is preferably an alkyl group or an aryl group from the viewpoint that the stability of the specific ultraviolet absorbing agent in an aqueous medium is better.

The two $R^3$'s in General Formula (3) are identical to each other.

In General Formula (3), the acid group contained in at least one group of $R^1$, $R^2$, or $R^3$ is selected from the group consisting of a sulfonic acid group, a carboxylic acid group, and a phosphoric acid group, and it is preferably a sulfonic acid group or a phosphoric acid group and more preferably a sulfonic acid group. The acid group may be in a salt state as described above.

The number of acid groups in the compound represented by General Formula (3) may be 1 or more, and the compound may have 2 or more acid groups. The upper limit of the number of acid groups is the same as the case of General Formula (1).

The number of acid groups in General Formula (3) is preferably 1 to 3 and more preferably 2 or 3 from the viewpoint that the solubility in water and the stability in an aqueous medium is better in the specific ultraviolet absorbing agent.

In a case where the specific ultraviolet absorbing agent represented by General Formula (3) has two or more acid groups, a plurality of acid groups may be the same or different from each other. For synthetic suitability, it is preferable that the plurality of acid groups are the same as each other.

Examples of the preferred combination of the substituents in General Formula (3) include a combination in which $R^1$ and $R^2$ are an alkyl group having a sulfonic acid group or an alkyl group having a phosphoric acid group and $R^3$ is an alkyl group or aryl group, a combination in which one of $R^1$ and $R^2$ is an alkyl group and the other is an alkyl group having a sulfonic acid group and one of $R^3$ is an alkyl group having a sulfonic acid group, a combination in which $R^1$ and $R^2$ are an alkyl group and both $R^3$ is an alkyl group having a sulfonic acid group or a phosphoric acid group.

[Compound Represented by General Formula (4)]

In the present disclosure, the compound represented by General Formula (4) is a novel compound.

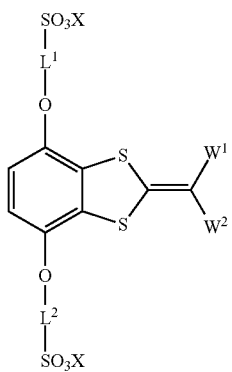

(4)

In General Formula (4), $L^1$ and $L^2$ each independently represent an alkylene group.

X's each independently represent a hydrogen atom or a countercation of $-SO_3^-$.

$W^1$ and $W^2$ each independently represent a hydrogen atom, a cyano group, a carbamoyl group, a sulfamoyl group, a nitro group, an acyl group, an alkylsulfonyl group, an arylsulfonyl group, an alkylsulfinyl group, an arylsulfinyl group, an alkoxycarbonyl group, an aryloxycarbonyl group, an alkyl group, an aryl group, or a heterocyclic group, where at least one of $W^1$ or $W^2$ represents a substituent having a Hammett's substituent constant σp value of 0.2 or more. $W^1$ and $W^2$ may be bonded to each other to form a ring.

$L^1$ and $L^2$ each independently represent an alkylene group, and they are preferably an alkylene group having 1 to 10 carbon atoms and more preferably an alkylene group having 2 to 5 carbon atoms.

X's each independently represent a hydrogen atom or a countercation of $-SO_3^-$, and the countercation is preferably an alkali metal ion such as a sodium ion, a potassium ion, or a lithium ion.

$W^1$ and $W^2$ each independently represent a hydrogen atom, a cyano group, a carbamoyl group, a sulfamoyl group, a nitro group, an acyl group, an alkylsulfonyl group, an arylsulfonyl group, an alkylsulfinyl group, an arylsulfinyl group, an alkoxycarbonyl group, an aryloxycarbonyl group, an alkyl group, an aryl group, or a heterocyclic group, where at least one of $W^1$ or $W^2$ represents a substituent having a Hammett's substituent constant σp value of 0.2 or more. $W^1$ and $W^2$ may be bonded to each other to form a ring.

$W^1$ and $W^2$ are synonymous with $W^1$ and $W^2$ in the General Formula (1) described above, and the same applies to the preferred examples thereof.

The compound represented by General Formula (4) has an absorption maximum in a wavelength range of 380 nm to 400 nm and thus is useful as an ultraviolet absorbing agent.

Hereinafter, Exemplary Compounds (M-1) to (M-10) as specific examples of the compound represented by General Formula (2), where the compound is a preferred example of the compound represented by General Formula (1) and Exemplary Compounds (M-11) to (M-20) as specific examples of the compound represented by General Formula (3) are shown by specifying the general formula and the substituent in the general formula. It is noted that the specific ultraviolet absorbing agent in the present disclosure is not limited to Exemplary Compounds below.

The solubility of each compound in water at 25° C. is shown together (described as "solubility (25° C.)" in the table). The measuring method for the solubility in water (distilled water) is as described above.

In Exemplary Compounds below, "Me" indicates a methyl group, "Et" indicates an ethyl group, "Ph" indicates a phenyl group, "n-Bu" indicates a normal butyl group, and "t-Bu" indicates a tertiary butyl group.

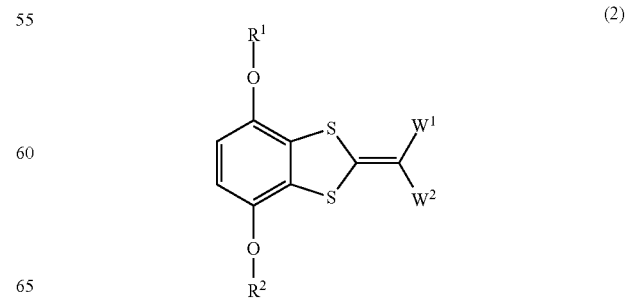

(2)

| | R¹ | R² | W¹ | W² | Solubility (25° C.) (% by mass) |
|---|---|---|---|---|---|
| M-1 | (CH₂)₄SO₃Na | (CH₂)₄SO₃Na | CN | —CO—t—Bu | 3.2 |
| M-2 | (CH₂)₃SO₃Na | (CH₂)₃SO₃Na | CN | —COPh | 2.9 |
| M-3 | (CH₂)₄SO₃Na | (CH₂)₄SO₃Na | CN | CN | 3.1 |
| M-4 | (CH₂)₄SO₃Na | n-Bu | CN | SO Ph | 3.0 |
| M-5 | (CH₂)₄SO₃Na | (CH₂)₄SO₃Na | CN | CH(=NOMe) | 3.1 |
| M-6 | (CH₂)₂SO₂Na | (CH₂)₂SO₃Na | —COPh-4-OMe | —COPh-4-OMe | 3,1 |
| M-7 | (CH₂)₄PO(OH)₂ | (CH₂)₄PO(OH)₂ | CN | CN | 2.0 |
| M-8 | CO(CH₂)₂CO₂Na | CO(CH₂)₂CO₂Na | CN | CN | 2.6 |
| M-9 | n-Bu | n-Bu | CN | —CO₂(CH₂)₄SO₃Na | 2.1 |
| M-10 | n-Bu | n-Bu | CN | —CO₂(CH₂)₄PO(OH)₂ | 1.9 |

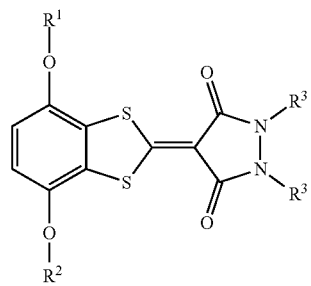

(3)

| | R¹ | R² | R³ | Solubility (25° C.) (% by mass) |
|---|---|---|---|---|
| M-11 | (CH₂)₄SO₃Na | (CH₂)₄SO₃Na | n-Bu | 3.4 |
| M-12 | (CH₂)₃SO₃Na | (CH₂)₃SO₃Na | n-Bu | 3.6 |
| M-13 | (CH₂)₄SO₃Na | (CH₂)₄SO₃Na | Ph | 3.3 |
| M-14 | (CH₂)₄SO₃Na | n-Bu | (CH₂)₄SO₃Na | 3.7 |
| M-15 | (CH₂)₂EtC₄H₉ | (CH₂)₂EtC₄H₉ | (CH₂)₄SO₃Na | 2.9 |
| M-16 | (CH₂)₂SO₃Na | (CH₂)₂SO₃Na | (CH₂)₃SO₃Na | 2.9 |
| M-17 | (CH₂)₄PO(OH)₂ | (CH₂)₄PO(OH)₂ | n-Bu | 3.0 |
| M-18 | CO(CH₂)₂CO₂H | CO(CH₂)₂CO₂H | n-Bu | 2.8 |
| M-19 | n-Bu | n-Bu | (CH₂)₄PO(OH)₂ | 3.0 |
| M-20 | n-Bu | n-Bu | (CH₂)₄CO₂Na | 2.9 |

Among the above-Exemplary Compounds, the compounds (M-1) to (M-3), (M-11) to (M-13), and (M-14) and (M-16) are preferable, and the compounds (M-3), (M-11), and (M-12) are more preferable, from the viewpoint that the solubility in water and the stability in an aqueous medium are better.

Among Exemplary Compounds described above, the compounds (M-1), (M-2), (M-3), (M-5), (M-6), (M-11), (M-12), (M-13), and (M-16) are novel compounds included in General Formula (4).

The specific ultraviolet absorbing agent has good ultraviolet absorbability at a wavelength of 380 nm to 400 nm and has good solubility in water and good stability in an aqueous medium, and thus aggregation or precipitation hardly occurs even in a case of being aged in an aqueous medium. Further, in a case where an ultraviolet absorbing composition containing the specific ultraviolet absorbing agent, a water-soluble polymer, and an aqueous medium is cured to form an ultraviolet absorbing film, the formed ultraviolet absorbing film has good transparency and the increase in haze caused by the aggregation or the precipitation of the specific ultraviolet absorbing agent in the ultraviolet absorbing film is suppressed.

The "haze" in the present disclosure can be measured using a haze meter.

As the haze meter, for example, a haze meter (manufactured by NIPPON DENSHOKU INDUSTRIES Co., Ltd., NDH4000: device name), a haze meter (manufactured by Suga Test Instruments Co., Ltd., HGM-2DP: device name), or the like can be used.

The specific ultraviolet absorbing agent of the present disclosure having a sulfonic acid group in the molecule can be synthesized by a method of reacting a cyclic sulfone with a hydroxy compound or amino compound having a corresponding benzothiolane skeleton under basic conditions.

In addition, the specific ultraviolet absorbing agent of the present disclosure having a carboxylic acid group in the molecule can be synthesized by a method of reacting an acid anhydride with a hydroxy compound or amino compound having a corresponding benzothiolane skeleton under basic conditions.

The detailed synthesis method will be described in Examples described later.

[Ultraviolet Absorbing Composition]

The ultraviolet absorbing composition of the present disclosure contains the above-described specific ultraviolet absorbing agent of the present disclosure and an aqueous medium.

The ultraviolet absorbing composition of the present disclosure may contain only one kind of the above-described specific ultraviolet absorbing agent or may contain two or more kinds thereof.

The content of the specific ultraviolet absorbing agent with respect to the total amount of the ultraviolet absorbing composition can be appropriately selected depending on the intended purpose.

Among the above, the content of the specific ultraviolet absorbing agent with respect to the total amount of the ultraviolet absorbing composition is preferably 0.05% by mass to 5.0% by mass and more preferably 0.10% by mass to 3.0% by mass.

In a case where the content of the specific ultraviolet absorbing agent is 0.05% by mass or more, sufficient ultraviolet absorbability is obtained with the ultraviolet absorbing composition, and in a case where it is 5.0% by mass or less, the generation of turbidity, the increase in haze, and the like due to the precipitation or the aggregation of the specific ultraviolet absorbing agent in the ultraviolet absorbing composition and the cured substance of the ultraviolet absorbing composition are more effectively suppressed.

Since the above-described specific ultraviolet absorbing agent of the present disclosure has good solubility in water and good stability in an aqueous medium, the ultraviolet absorbing composition of the present disclosure is also excellent in aging-associated stability. More specifically, even in a case where the ultraviolet absorbing composition of the present disclosure (hereinafter, may be simply referred to as a "composition of the present disclosure" or a "composition") is aged in an aqueous medium, the decrease in the ultraviolet absorbability of the ultraviolet absorbing composition, the change in appearance, and the like, which are caused by the aggregation or the precipitation of the specific ultraviolet absorbing agent of the present disclosure, are suppressed.

(Aqueous Medium)

The "aqueous medium" in the present disclosure refers to water and a mixture of water and a water-soluble organic solvent.

The aqueous medium functions as a solvent for the specific ultraviolet absorbing agent.

Examples of the water-soluble organic solvent that can be contained in the aqueous medium include a monohydric alcohol having 1 to 3 carbon atoms (methanol, ethanol, propanol, or the like), a polyhydric alcohol having 1 to 4 carbon atoms (diethylene glycol, glycerin, or the like), tetrahydrofuran, acetonitrile, and dimethylsulfoxide.

Only one kind of water-soluble organic solvent that is used by mixing with water may be used, and two or more kinds thereof can be used as necessary.

Examples of the aqueous medium that can be used in the ultraviolet absorbing composition of the present disclosure include water, a mixture of water and a monovalent alcohol having 1 to 3 carbon atoms, and acetonitrile.

From the viewpoint of the stability of the specific ultraviolet absorbing agent in the ultraviolet absorbing composition, water or a mixture of water and a monohydric alcohol having 1 to 3 carbon atoms (hereinafter, may be referred to as a lower alcohol) is preferable, and water is more preferable.

The water as an aqueous medium is not particularly limited, and tap water may be used. Among the above, distilled water, ion exchange water, pure water, or the like is preferably used as the water from the viewpoint of having few impurities.

Regarding the mixture of water and a lower alcohol, the mixing ratio of water/lower alcohol can be 20/80 to 99/1 in terms of mass ratio.

In addition to the specific ultraviolet absorbing agent and the aqueous medium, the ultraviolet absorbing composition of the present disclosure may further contain various components depending on the purpose of use of the composition. Examples of the other components that can be contained in the ultraviolet absorbing composition of the present disclosure include a water-soluble polymer, a coloring agent, a viscosity-adjusting agent other than the water-soluble polymer, a crosslinking agent, and a leveling agent.

(Water-Soluble Polymer)

The ultraviolet absorbing composition of the present disclosure can include a water-soluble polymer. In a case where the composition of the present disclosure contains a water-soluble polymer, the viscosity of the composition can be adjusted depending on the intended purpose. Further, the film forming property can be imparted to the composition by selecting the water-soluble polymer to be used.

As the water-soluble polymer that can be used in the composition of the present disclosure, a polymer having solubility in the above-described aqueous medium is used.

The "water-soluble polymer" in the present disclosure refers to a polymer, 0.1% by mass or more of which is dissolved in distilled water at 25° C. It is preferable that 1% by mass or more of the water-soluble polymer is dissolved in distilled water at 25° C., and it is more preferably that 3.0% by mass or more thereof is dissolved in distilled water at 25° C.

The water-soluble polymer is not particularly limited as long as it has water solubility, and can be appropriately selected from known polymers depending on the intended purpose.

Examples of the water-soluble polymer include an acrylic polymer having an acidic group; polyvinyl ether/maleic anhydride polymers described in JP1971-2121A (JP-S46-2121A), JP1981-40824B (JP-S56-40824B), and the like; a water-soluble salt of carboxyalkyl cellulose; water-soluble cellulose ethers; a water-soluble salt of carboxyalkyl starch; polyvinyl alcohol; a polyvinyl alcohol derivative such as water-soluble polyvinyl butyral or water-soluble polyvinyl acetal; polyvinylpyrrolidone; various polyacrylamides; various water-soluble polyamides such as poly-2-acrylamide-2-methylpropanesulfonic acid; a water-soluble salt of polyacrylic acid; gelatin; an ethylene oxide polymer such as polyethylene oxide or polypropylene oxide; a water-soluble salt of the group consisting of various starches and analogs thereof; a polystyrene-4-sulfonate; a copolymer of styrene/maleic acid; and a maleinate resin.

Among them, the water-soluble polymer is preferably an acrylic polymer having an acid group, polyvinyl alcohol, or a derivative thereof, and specifically, an acrylic polymer having an acidic group, polyvinyl butyral, polyvinyl acetal, completely saponified polyvinyl alcohol, or polyvinyl alcohol obtained by partially saponifying polyvinyl acetate is more preferable.

The weight-average molecular weight of the water-soluble polymer is preferably 1 million or less, more preferably 1,000 to 1 million, and most preferably 2,000 to 100,000.

The weight-average molecular weight of the water-soluble polymer can be measured by the following method with a gel permeation chromatography (GPC) method or the like using an aqueous eluent (for example, tetrahydrofuran or the like).

The weight-average molecular weight of the water-soluble polymer in the present disclosure is measured by gel permeation chromatography (GPC) as a polystyrene-equivalent value under the following conditions. The calibration curve can be created using eight samples of "Standard sample TSK standard, polystyrene": "F-40", "F-20", "F-4", "F-1", "A-5000", "A-2500", "A-1000", and "n-propylbenzene", manufactured by Tosoh Corporation.

<Conditions>

GPC: HLC (registered trade mane) −8020GPC (manufactured by Tosoh Corporation)

Column: G3000HXL and G2000HXL

Eluent: An eluent can be selected from THF (tetrahydrofuran), chloroform, NMP (N-methyl-2-pyrrolidone), and m-cresol/chloroform (manufactured by Shonan Wako Pure Chemical Industries, Ltd.), and THF is used as the eluent in a case where a water-soluble polymer dissolves in THF.

Sample concentration: 0.45% by mass

Flow rate: 1 milliliters/min (mL/min)

Sample injection volume: 10 microliters (μL)

Measurement temperature: 23° C.

A differential refractometer (RI) detector is used.

In a case where the composition of the present disclosure contains a water-soluble polymer, the content of the water-soluble polymer is appropriately selected depending on the purpose of use of the composition.

In a case where the composition of the present disclosure contains a water-soluble polymer, only one kind of water-soluble polymer may be contained, or two or more kinds thereof may be contained.

For example, in a case of adjusting the viscosity of the composition, at least any one of the kind or the adding amount of the aqueous medium and the water-soluble polymer may be appropriately adjusted in order to obtain the desired viscosity.

Further, for example, in a case where an ultraviolet absorbing film is formed from the composition of the present disclosure, the water-soluble polymer is preferably 0.1% by mass to 50% by mass and more preferably 1% by mass to 20% by mass with respect to the total amount of the composition.

(Coloring Agent)

The ultraviolet absorbing composition of the present disclosure can contain a coloring agent.

In the composition of the present disclosure, examples of the coloring agent that may be used in combination with the specific ultraviolet absorbing agent include a pigment and a dye.

Preferred examples of the pigment include inorganic pigments such as titanium oxide, zinc oxide, carbon black, aluminum powder-based pigment, ferric oxide (red iron oxide), lead chromate, molybdate orange, yellow lead, yellow iron oxide, ocher, ultramarine, and cobalt green; and organic pigments such as an azo-based pigment, a naphthol-based pigment, a pyrazolone-based pigment, an anthraquinone-based pigment, a perylene-based pigment, a quinacridone-based pigment, a disazo-based pigment, an isoindolinone-based pigment, a benzimidazole-based pigment, a phthalocyanine-based pigment, and a quinophthalone-based organic pigment.

Preferred examples of the dye include organic dyes such as an anthraquinone-based dye, a quinophthalone-based dye, a methine-based dye, a phthalocyanine-based dye, and a perylene-based dye.

In a case of containing a coloring agent, the composition of the present disclosure may contain only one kind of coloring agent or may contain two or more kinds thereof.

The preferred coloring agent in a case where the composition of the present disclosure is applied to an aqueous paint will be described in detail below.

Since the composition of the present disclosure contains the specific ultraviolet absorbing agent having absorption at a wavelength of 380 nm to 400 nm and is excellent in stability, it is used for various use applications.

Since the composition of the present disclosure contains an aqueous medium and does not necessarily require to contain a volatile organic solvent, it can be used as a composition for forming an ultraviolet absorbing film, an aqueous paint, or a cosmetic material for skin or hair, which has a low burden on the environment.

Further, in a case where the composition of the present disclosure is cured, it is possible to obtain an ultraviolet absorbing film described later.

A known component can be appropriately selected depending on the intended purpose and can be contained in the composition of the present disclosure in addition to the specific ultraviolet absorbing agent, the aqueous medium, the water-soluble polymer which is a preferred optional component, and the coloring agent. Examples of the optional component other than the water-soluble polymer and the coloring agent, which can be contained in the composition of the present disclosure, similarly include an optional component that can be contained in the aqueous paint described later.

(Aqueous Paint)

Hereinafter, a preferred aspect in a case where the composition of the present disclosure is applied to an aqueous paint will be described.

The composition of the present disclosure can be applied to an aqueous paint.

The aqueous paint preferably contains a specific ultraviolet absorbing agent, an aqueous medium, a water-soluble polymer, and a coloring agent.

The coloring agent may be a dye or a pigment.

As the water-soluble polymer, the water-soluble polymer described in the section of the composition of the present disclosure described above is preferably used.

In a case where the composition of the present disclosure is used as an aqueous paint, it is preferable to contain a crosslinking agent from the viewpoint of further improving the stability of the coating film to be formed.

The crosslinking agent that can be used in the aqueous paint is preferably an alkoxide compound of a metal selected from Si, Ti, Zr, and Al. The metal alkoxide that is used in the aqueous paint is a hydrolytically polymerizable compound that has a functional group capable of being hydrolyzed and polycondensed in structure thereof and functions as a crosslinking agent, and the metal alkoxides are polycondensed with each other to form a strong crosslinked film having a crosslinked structure and are further chemically bonded to the above-described hydrophilic polymer as well.

Examples of the metal alkoxide include compounds represented by General Formula (VI-1) and General Formula (VI-2).

$(R^8)_m-Z-(OR^9)_{4-m}$ (VI-1)

$Al-(OR^9)_3$ (VI-2)

In Formula (VI-1) or (VI-2), $R^8$ represents a hydrogen atom, an alkyl group, or an aryl group, $R^9$ represents an alkyl group or an aryl group, Z represents Si, Ti, or Zr, and m represents an integer of 0 to 2.

In a case where $R^8$ and $R^9$ each independently represent an alkyl group, the alkyl group preferably has 1 to 4 carbon atoms.

The alkyl group or the aryl group may have a substituent, and examples of the substituent introduceable thereto include a halogen atom, an amino group, and a mercapto group. The metal alkoxide compound that can be used as a crosslinking agent is preferably a low-molecular-weight compound having a molecular weight of 2,000 or less.

Hereinafter, specific examples of the hydrolyzable metal alkoxide compound represented by General Formula (VI-1) or General Formula (VI-2) will be described; however, the present disclosure is not limited thereto.

In General Formula (VI-1), in a case where Z is Si, that is, in a case where a compound contains silicon in the metal alkoxide compound as a crosslinking agent, examples of the compound include trimethoxysilane, tetramethoxysilane, tetraethoxysilane, tetrapropoxysilane, methyltrimethoxysilane, dimethyldimethoxysilane, γ-chloropropyltriethoxysilane, γ-mercaptopropyltrimethoxysilane, γ-aminopropyltriethoxysilane, phenyltrimethoxysilane, and diphenyldimethoxysilane. Among these, particularly preferred examples thereof include trimethoxysilane, tetramethoxysilane, tetraethoxysilane, methyltrimethoxysilane, dim ethyl di m ethoxysilane, and phenyltrimethoxysilane.

In a case where Z is Ti, that is, in a case where a compound contains titanium in the metal alkoxide compound as a crosslinking agent, examples of the compound include trimethoxy titanate, tetramethoxy titanate, triethoxy titanate, tetraethoxy titanate, tetrapropoxytitanate, chlorotrimethoxy titanate, chlorotriethoxy titanate, ethyltrimethoxy titanate, methyltriethoxy titanate, ethyltriethoxy titanate, diethyldiethoxy titanate, phenyltrimethoxy titanate, and phenyltriethoxy titanate.

In a case where Z is Zr, that is, in a case where a compound contains zirconium in the metal alkoxide compound as a crosslinking agent, examples of the compound include zirconates corresponding to the compounds exemplified as the compounds containing titanium.

In addition, in a case where the metal alkoxide compound as a crosslinking agent is a compound having Al as a central metal, which is represented by General Formula (VI-2), that is, in a case where a compound contains aluminum in the metal alkoxide as a crosslinking agent, examples of the compound include trimethoxy aluminate, triethoxy aluminate, tripropoxy aluminate, and triisopropoxy aluminate.

In a case where an alkoxide compound of a metal selected from Si, Ti, Zr, and Al is used as a crosslinking agent in an aqueous paint, the content of the metal alkoxide compound is 1% by mass to 80% by mass and more preferably 5% by mass to 70% by mass with respect to the total solid content of the aqueous paint. The "total solid content" is the total amount of the components excluding the solvent contained in the aqueous paint, and even in a case where a water-soluble polymer or the like is present in the aqueous medium with being dissolved, it is included in the solid content.

In a case of containing a crosslinking agent, the aqueous paint may contain only one kind of crosslinking agent or may contain two or more kinds thereof.

The aqueous paint may further contain particles.

The particles that can be contained in the aqueous paint are particles consisting of an inorganic substance, an organic substance, or an inorganic substance and an organic substance, and are a solid content having a spherical shape, a flat shape, a rod shape, or the like.

The size of the particles that can be used in the aqueous paint is not particularly limited, but the particle size is preferably in a range of 10 nm to 10 µm from the viewpoint of maintaining the film quality of the coating film formed by using the aqueous paint.

The particle diameter of the particles in the present disclosure refers to the longest diameter in the projection view of particles in any of the cases of spherical particles, flat particles, rod-shaped particles, or the like.

Examples of the measuring method for the average particle diameter of particles include a method in which a coating film of an aqueous paint is observed with an optical microscope at a magnification of 50 to 100 times, and diameters of 20 particles in a viewing angle are measured and arithmetically averaged.

In a case where the aqueous paint contains particles, it can be expected that effects such as improvement of hydrophilicity, prevention of fissuring of the film formed from the aqueous paint, improvement of film hardness, and the like are exhibited.

Specific examples of the particles include inorganic particles consisting of an inorganic substance such as an inorganic pigment, silica, alumina, magnesium, or titanium, calcium, organic particles consisting of an organic substance such as acrylic, styrene, vinyl acetate, butadiene, chloroprene, ethylene, vinyl chloride, an alkylene oxide or the like, and composite particles having a coating layer consisting of an organic substance on the surface of the inorganic particles.

In a case of containing particles, the aqueous paint may contain only one kind of particle or may contain two or more kinds thereof.

The aqueous paint may contain a surfactant.

Examples of the surfactant that can be used in the aqueous paint include those described in JP1987-173463A (JP-S62-173463A) and JP1987-183457A (JP-62-183457A).

Examples of the surfactant include anionic surfactants such as dialkyl sulfosuccinates, alkylnaphthalene sulfonates, and fatty acid salts, nonionic surfactants such as polyoxyethylene alkyl ethers, polyoxyethylene alkyl allyl ethers, acetylene glycols, and polyoxyethylene/polyoxypropylene block copolymers, and cationic surfactants such as alkyl amine salts and quaternary ammonium salts.

Further, a fluorine-based compound such as an organic fluorocompound may be used as the surfactant or instead of the surfactant. The organic fluorocompound is preferably hydrophobic.

Examples of the organic fluorocompound in the present disclosure include a fluorine-based surfactant, an oily fluorine-based compound (for example, fluorine oil), and a solid-like fluorine compound resin (for example, a tetrafluoroethylene resin). More specific examples of the organic fluorocompound include the compounds described in JP1982-9053B (JP-S57-9053B) (columns 8 to 17) and JP1987-135826A (JP-S62-135826A).

In a case of containing a surfactant, the aqueous paint may contain only one kind of surfactant or may contain two or more kinds thereof.

The aqueous paint may contain an antioxidant.

In a case where the aqueous paint contains an antioxidant, the stability as the aqueous paint composition is further improved.

Examples of the antioxidant include EP223739A, EP309401A, EP309402A, EP310551A, EP310552A, EP459416A, GP3435443A, JP-1979A-262047A (JP-S54-262047A), JP1988-113536A (JP-S63-113536A), JP1988-163351A (JP-S63-163351A), JP1990-262654A (JP-H2-262654A), JP1990-71262A (JP-H2-71262A), JP1991-121449A (JP-H3-121449A), JP1993-61166A (JP-H5-61166A), JP1993-119449A (JP-H5-119449A), U.S. Pat. Nos. 4,814,262A, and 4,980,275A.

In a case of containing an antioxidant, the aqueous paint may contain only one kind of antioxidant or may contain two or more kinds thereof.

The aqueous paint may contain an organic solvent other than the aqueous medium as long as the effect thereof is not impaired.

In a case where an organic solvent is contained, it can be expected that the film forming property of a uniform coating film on a substrate is further improved in a case where the coating film is formed from the composition.

Examples of the organic solvent other than the aqueous medium include a ketone-based solvent such as acetone, methyl ethyl ketone, or a diethyl ketone, a chlorine-based solvent such as chloroform or methylene chloride, an aromatic solvent such as benzene or toluene, an ester-based solvent such as ethyl acetate, butyl acetate, or isopropyl acetate, an ether-based solvent such as diethyl ether, and a glycol ether-based solvent such as ethylene glycol monomethyl ether or ethylene glycol dimethyl ether.

In order to adjust the physical properties of the coating film, it is possible for the aqueous paint to contain a polymer compound other than the water-soluble polymer described above as long as hydrophilicity is not impaired.

Examples of the other polymer compound include an acrylic polymer which contains no acid group, a polyurethane resin, a polyamide resin, a polyester resin, an epoxy resin, a phenolic resin, a polycarbonate resin, a polyvinyl formal resin, shellac, a vinyl resin which contains no acid group, a rubber-based resin, waxes, and other natural resins.

In a case where the aqueous paint contains another polymer compound, it is preferable that the other polymer compound includes a vinyl-based copolymer obtained by copolymerizing an acrylic-based monomer.

In a case of containing another polymer compound, the aqueous paint may contain only one kind of the other polymer compound or may contain two or more kinds thereof.

The aqueous paint may contain a known coloring agent generally used in the aqueous paint, in order to adjust the color tone of the coating film of the aqueous paint.

The coloring agent is not particularly limited and may be a dye or a pigment. Among the above, a pigment is preferable from the viewpoint of light fastness and durability.

Examples of the pigment that can be used in the aqueous paint include inorganic pigments such as titanium oxide, zinc oxide, carbon black, aluminum powder-base pigment, ferric oxide (red iron oxide), lead chromate, molybdate orange, yellow lead, yellow iron oxide, ocher, ultramarine, and cobalt green; and organic pigments such as an azo-based pigment, a naphthol-based pigment, a pyrazolone-based pigment, an anthraquinone-based pigment, a perylene-based pigment, a quinacridone-based pigment, a disazo-based pigment, an isoindolinone-based pigment, a benzimidazole-based pigment, a phthalocyanine-based pigment, and a quinophthalone-based organic pigment.

The aqueous paint may contain an extender pigment such as heavy calcium carbonate, clay, kaolin, talc, precipitated barium sulfate, barium carbonate, white carbon, and diatomaceous earth. In particular, in a case where a matte coating film is formed from the aqueous paint on the surface of a base material, it is preferable to use white carbon or diatomaceous earth as the extender pigment, which has the least damage to the non-contamination effect on the coating film surface.

In a case where inorganic particles such as an extender pigment or an inorganic pigment are contained in the aqueous paint, it is also possible to take measures such as treating the surface of the pigment with a coupling agent, adding a coupling agent to the aqueous paint, or the like, for the intended purpose of further improving the uniform dispersibility in the aqueous medium or the like.

In a case of containing a coloring agent, the aqueous paint may contain only one kind of coloring agent or may contain two or more kinds thereof depending on the intended purpose.

The content of the pigment in the aqueous paint is appropriately adjusted depending on the intended purpose. From the viewpoints of the colorability of the coating film to be formed (for example, the covering property of the base material) and the uniformity of the coating film, the content of the pigment is preferably 0.1% by mass to 20% by mass with respect to the total solid content of the aqueous paint. The content of the pigment is more preferably 1% by mass to 10% by mass with respect to the total solid content of the aqueous paint from the viewpoint that all of the pigment effect, the hydrophilicity, and the film hardness of the pigment are better.

The particle diameter of the pigment is not particularly limited; however, it is preferably 0.01 µm to 100 µm and more preferably 0.1 µm to 10 µm from the viewpoint of film hardness. The particle diameter of the pigment can be measured in the same manner as the particle diameter of the particles that can be contained in the aqueous paint described above.

The aqueous paint may contain an ultraviolet absorbing agent other than the specific ultraviolet absorbing agent as long as the effect thereof is not impaired. Hereinafter, the ultraviolet absorbing agent other than the specific ultraviolet absorbing agent may be referred to as another ultraviolet absorbing agent.

Examples of the other ultraviolet absorbing agent that can be contained in the aqueous paint include benzotriazole-based compounds described in JP1983-185677A (JP-S58-185677A), JP1986-190537A (JP-S61-190537A), JP1990-782A (JP-H2-782A), JP1993-197075A (JP-H5-197075A), JP1997-34057A (JP-H9-34057A), and the like; benzophenone-based compounds described in JP1971-2784A (JP-S46-2784A), JP1993-194483A (JP-H5-194483A), U.S. Pat. No. 3,214,463A, and the like; cinnamic acid-based compounds described in JP1973-30492A (JP-S48-30492A), JP1981-21141A (JP-S56-21141A), JP1998-88106A (JP-H10-88106A), and the like; triazine-based compounds described in JP1992-298503A (JP-H4-298503A), JP1996-53427A (JP-H8-53427A), JP1996-239368A (JP-H8-239368A), JP1998-182621A (JP-H10-182621A), JP1996-501291A (JP-H8-501291A), and the like; compounds, so-called fluorescent whitening agents, which absorb ultraviolet rays and emits fluorescence, which are represented by a compound described in Research Disclosure No. 24239, a stilbene-based compound, and a benzoxazole-based compound.

As the kind of the other ultraviolet absorbing agent that can be contained in the aqueous paint, a benzotriazole-based compound, a benzophenone-based compound, or a benzoxazole-based compound is preferable.

The content of the other ultraviolet absorbing agent in the aqueous paint of the present disclosure is not particularly limited. The content of the other ultraviolet absorbing agent is preferably in a range of 10% by mass to 100% by mass and more preferably in a range of 50% by mass to 80% by mass with respect to the specific ultraviolet absorbing agent.

In a case where the aqueous paint contains the other ultraviolet absorbing agent other than the specific ultraviolet absorbing agent, it may contain only one kind of other ultraviolet absorbing agent or may contain two or more kinds thereof.

In addition to the above-described essential components and preferred optional components, the aqueous paint may further contain a component that can be used in the general paint.

Examples of another component include an aggregate, a viscosity improver, a film-forming aid, a leveling agent, a wetting agent, a plasticizer, an antifreezing agent, a pH adjusting agent, a preservative, a fungicide, an antialgae agent, a dispersing agent, an antifoaming agent, and a rust inhibitor.

The composition of the present disclosure can be applied to various use applications such as a composition for forming an ultraviolet absorbing film, an aqueous paint, and a cosmetic material for skin or hair.

[Ultraviolet Absorbing Film]

The ultraviolet absorbing film of the present disclosure is a cured substance of the above-described ultraviolet absorbing composition.

The manufacturing method for the ultraviolet absorbing film of the present disclosure is not particularly limited, and a known film forming method can be applied.

Examples of the film forming method include a method of molding an ultraviolet absorbing composition having an adjusted viscosity into a film shape by an extrusion method or the like and then curing the formed film, a method of applying an ultraviolet absorbing composition onto a base material to form a film of the ultraviolet absorbing composition and curing the film, and a method of immersing a base material in an ultraviolet absorbing composition to form a film of an ultraviolet absorbing composition and curing the film.

The curing of a film consisting of an ultraviolet absorbing composition can be carried out by any method, for example, by reducing a solvent contained in the film of the ultraviolet absorbing composition with drying, applying energy such as light or heat to a film of an ultraviolet absorbing composition containing a crosslinking agent to form a crosslinked structure in the film with a crosslinking agent, or cooling a film of an ultraviolet absorbing composition containing gelatin or the like as a water-soluble polymer to cure the film by lowering the temperature by a sol-gel reaction.

The thickness of the ultraviolet absorbing film is appropriately selected depending on the intended purpose.

In a case of a transparent ultraviolet absorbing film, the thickness of the ultraviolet absorbing film can be set to 0.01 μm to 1000 μm, and it is preferably in a range of 0.1 μm to 100 μm from the viewpoint that ultraviolet rays having a wavelength of 380 nm to 400 nm can be sufficiently absorbed and the transparency is good.

Further, the thickness of the ultraviolet absorbing film is not limited to the above range. For example, in a case where the ultraviolet absorbing film is formed from an ultraviolet absorbing composition containing a coloring agent such as an aqueous paint, the thickness may be appropriately adjusted in consideration of the covering property of the base material.

The ultraviolet absorbing film of the present disclosure can absorb ultraviolet rays having a wavelength of 380 nm to 400 nm, has a low haze, has good transparency, and the increase in haze, which is caused by the aggregation or the precipitation of the specific ultraviolet absorbing agent, is suppressed, and the durability is good even after aging.

In the present disclosure, the haze is evaluated by the degree of turbidity in a case where the ultraviolet absorbing film of the present disclosure, which is a cured substance of the ultraviolet absorbing composition, is observed. Regarding the increase in haze due to aging, the measured value of the initial haze of the ultraviolet absorbing film is compared with the measured value of the haze after aging, and then it is evaluated that the haze is increased due to aging in a case where turbidity occurs or the degree of turbidity is increased due to aging, and the measured value of haze after aging is increased with respect to the measured value of the initial haze.

The measuring method for a haze is as described above.

The haze of the ultraviolet absorbing film of the present disclosure is preferably 2% or less and more preferably 1% or less in a film thickness of 0.01 μm to 1,000 μm.

Since the ultraviolet absorbing film of the present disclosure is a hydrophilic film, it can be used for various use applications that require hydrophilicity.

[Laminate]

The laminate of the present disclosure has a base material and the above-described ultraviolet absorbing film of the present disclosure formed on the base material.

The base material is not particularly limited, and any base material on which the ultraviolet absorbing film of the present disclosure can be formed can be used. Examples of the base material include inorganic base materials such as a glass plate, a metal plate, and a gypsum board, and organic base materials such as a resin plate.

Since the ultraviolet absorbing film of the present disclosure has good absorbency at a wavelength of 380 nm to 400 nm and a low haze, it is also preferable to use a transparent base material. In addition, it is also preferable to use an ultraviolet absorbing film to reduce the influence of ultraviolet rays on the base material, and in a case where an ultraviolet absorbing film is used to reduce the influence of ultraviolet rays, the base material does not necessarily have to be a transparent base material. For example, any molded body can be used as the base material.

In a case where the ultraviolet absorbing film of the present disclosure described above is a coating film (a cured substance) of an aqueous paint, the base material (the molded body) onto which the aqueous paint is applied becomes the base material of the laminate of the present disclosure.

Examples of the laminate include a laminate having an ultraviolet absorbing film on the surface of a glass base material. The laminate of the present disclosure having a glass base material can be used, for example, for a window glass of a house or a window glass or windshield of a vehicle such as an automobile. Further, it is also possible to form a laminate having an ultraviolet absorbing film between two glass plates. For example, in a case where an ultraviolet absorbing film is included between two laminated glasses, the durability of the ultraviolet absorbing film is further improved.

Further, in a case where an ultraviolet absorbing film, which is a cured substance of a coating film of an aqueous paint, is provided on the surface of various molded bodies, the laminate of the present disclosure has any color tone due to the aqueous paint, has a coating film excellent in ultraviolet shielding property, and thus becomes a laminate in which both surface decoration and shielding of ultraviolet rays on the long wavelength side of 380 nm to 400 nm are achieved.

EXAMPLES

Hereinafter, the present disclosure will be described more specifically with reference to Examples, but the present disclosure is not limited to the following Examples as long as the gist of the present invention is not exceeded.

Unless otherwise specified, "%" and "part" in Examples below are based on the mass.

A structure of a specific ultraviolet absorbing agent obtained by synthesis was confirmed by NMR.

The maximum absorption wavelength and the solubility in distilled water (25° C.) were measured by the methods described above.

The molar absorption coefficient was measured by the following method.

After dissolving 1.0 mg of a sample in 100 mL of pure water, the absorbance of the aqueous solution was measured in a 1 cm cell using a spectrophotometer (model number: UV 3150) manufactured by Shimadzu Corporation. From the measurement results, the molar absorption coefficient was calculated from the value of the absorbance at the maximum absorption wavelength using the Lambert-Beer law.

[Synthesis of Compound M-3]

Compound M-3, which is a specific ultraviolet absorbing agent, was synthesized by the following scheme. A raw material M-3A was synthesized by the method described in the document (Chem. Crystallography, 1997, Vol. 27, pp. 515-526). The compound M-3 is Exemplary Compound M-3 described above.

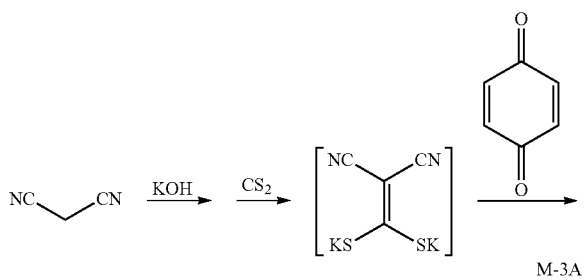

Specifically, 2.5 g of the raw material M-3A, 0.81 g of sodium hydroxide (manufactured by Tokyo Chemical Industry Co., Ltd.), and 3.0 g of 1,4-butane salton (manufactured by Tokyo Chemical Industry Co., Ltd.) were dissolved in 50 mL of ethanol, and then reflux stirring was carried out for 2 hours, the reaction solution was cooled to 25° C., and the precipitated crystals were filtered and separated.

The filtered and separated crystals were washed with methanol cooled to 0° C. and dried at room temperature to obtain 2.6 g of a target compound M-3 as a white powder.

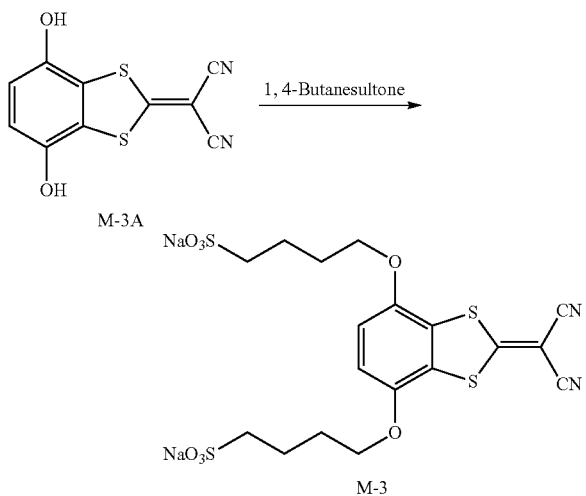

The analysis results of the obtained compound M-3 are as follows.

$^1$H-NMR (DMSO-d6) δ1.6-1.9 (m, 8H), 2.3-2.5 (m, 4H), 4.0-4.2 (m, 4H), 7.2 (s, 2H)

Maximum absorption wavelength: 372 nm ($H_2O$)
Molar absorption coefficient: 28,100
Solubility in distilled water (25° C.): 3.1% by mass

[Synthesis of Compound M-11]

Compound M-11, which is a specific ultraviolet absorbing agent, was synthesized by the following scheme. A raw material M-11A was synthesized by the method described in Example 1 of WO2019/065043A. The compound M-11 is Exemplary Compound M-11.

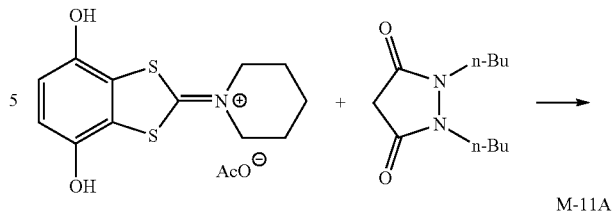

Specifically, 3.9 g of the raw material M-11A, 0.81 g of sodium hydroxide (manufactured by Tokyo Chemical Industry Co., Ltd.), and 3.0 g of 1,4-butane salton (manufactured by Tokyo Chemical Industry Co., Ltd.) were dissolved in 50 mL of ethanol, and then reflux stirring was carried out for 2 hours, the reaction solution was cooled to 25° C., and the precipitated crystals were filtered and separated. The filtered and separated crystals were washed with methanol cooled to 0° C. and dried at room temperature to obtain 5.6 g of a target compound M-11 as a white powder.

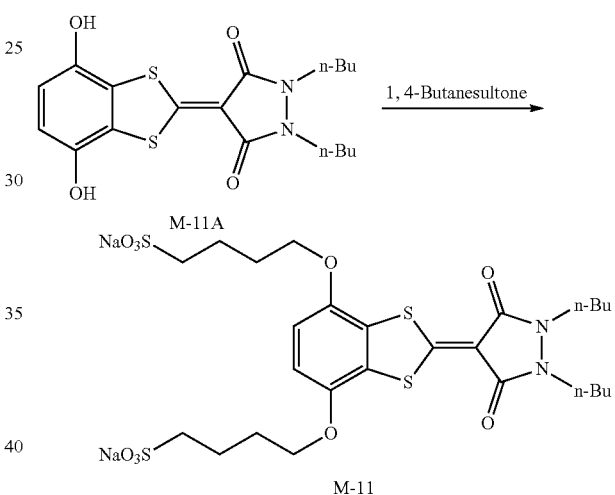

The analysis results of the obtained compound M-11 are as follows.

$^1$H-NMR (DMSO-d6) δ 0.86 (t, 6H), 1.2-1.4 (m, 8H), 1.5-1.6 (m, 4H), 1.8-1.9 (m, 4H), 2.3-2.5 (m, 4H), 3.6-3.8 (m, 4H), 4.0-4.2 (m, 4H), 7.2 (s, 2H)

Maximum absorption wavelength: 387 nm ($H_2O$)
Molar absorption coefficient: 35,900
Solubility in distilled water (25° C.): 3.4% by mass

[Synthesis of Compound M-5]

Compound M-5, which is a specific ultraviolet absorbing agent, was synthesized by the following scheme.

3.0 g of the raw material M-3A, 1.0 g of sodium hydroxide (a product manufactured by Tokyo Chemical Industry Co., Ltd.), and 3.5 g of 1,4-butane salton (a product manufactured by Tokyo Chemical Industry Co., Ltd.) were dissolved in 50 mL of methanol, and then reflux stirring was carried out for 2 hours, the reaction solution was cooled to 25° C., and the precipitated crystals were filtered and separated. The filtered and separated crystals were washed with methanol cooled to 0° C. and dried at room temperature to obtain 3.6 g of a target compound M-5 as a white powder. The compound M-5 is Exemplary Compound M-5.

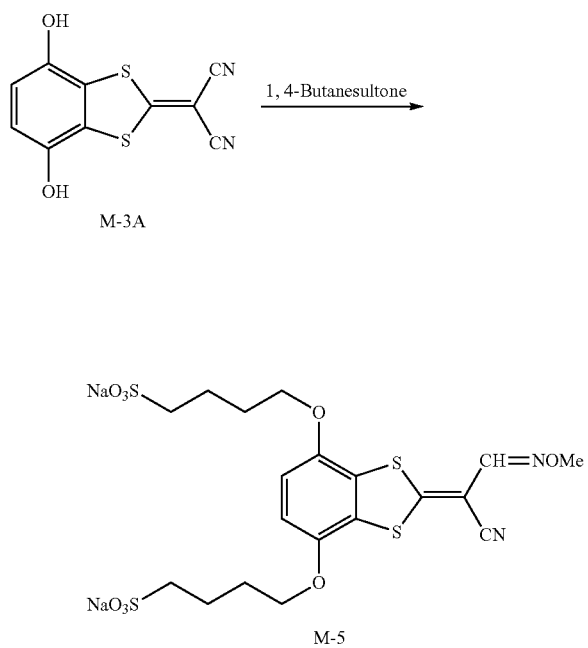

M-3A 1,4-Butanesultone

M-5

The analysis results of the obtained compound M-5 are as follows.

$^1$H-NMR (DMSO-d6) δ 1.6-1.9 (m, 8H), 2.3-2.5 (m, 4H), 3.7 (s, 3H), 4.0-4.3 (m, 4H), 7.15 (s, 2H), 8.0 (s, 1H)

Maximum absorption wavelength: 390 nm (H$_2$O)

Molar absorption coefficient: 27,400

Solubility in distilled water (25° C.): 3.1% by mass

[Synthesis of Compound M-18]

3.0 g of the raw material M-3A, 1.0 g of triethylamine (a product manufactured by Tokyo Chemical Industry Co., Ltd.), and 2.5 g of succinic anhydride (a product manufactured by Tokyo Chemical Industry Co., Ltd.) were dissolved in 50 mL of acetonitrile, and then reflux stirring was carried out for 2 hours, the reaction solution was cooled to 25° C., and 1 mL of acetic acid was added thereto. The precipitated crystals were filtered and separated. The filtered and separated crystals were washed with methanol cooled to 0° C. and dried at room temperature to obtain 3.2 g of a target compound M-18 as a white powder. The compound M-18 is Exemplary Compound M-18.

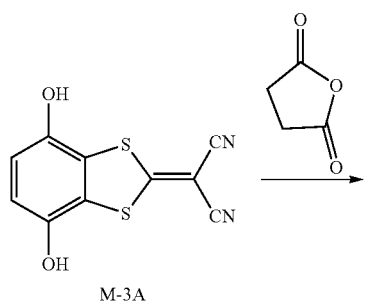

M-3A

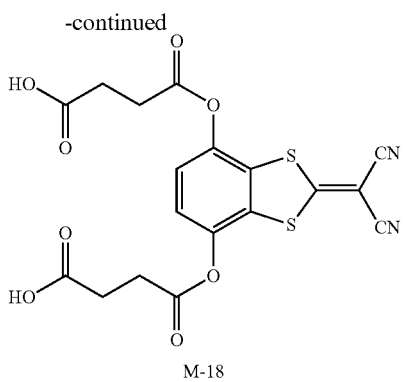

M-18

The analysis results of the obtained compound M-18 are as follows.

$^1$H-NMR (DMSO-d6) δ 2.1-2.4 (m, 8H), 7.20 (s, 2H), 10.5 (b, 2H) Maximum absorption wavelength: 385 nm (H$_2$O) Solubility in distilled water (25° C.): 2.8% by mass Example 1

5.0 parts by mass of the compound M-3, 45.0 parts by mass of polyvinyl alcohol (PVA), and 500 parts by mass of water were mixed, stirred at 40° C. for 1 hour to completely dissolve the mixture, whereby an ultraviolet absorbing composition of Example 1 was obtained. After cooling to room temperature, the obtained composition was applied onto a glass plate (size: 76 mm×52 mm×1 mm, product name; 59111, manufactured by Matsunami Glass Ind. Co., Ltd.) by the dip coating method to form a coating film, followed by drying on a hot plate at 100° C. for 20 seconds to form an ultraviolet cured film which is a cured substance of the ultraviolet absorbing composition. The coating amount of one dip coating was 0.3 g/cm$^2$ (the film thickness after drying was 300 μm).

The dip coating and drying were repeated 5 times to obtain a laminate having an ultraviolet absorbing film having a film thickness of 1.5 mm on a base material which is a glass plate.

The thickness of the laminate was 2.5 mm.

[Performance Evaluation]

The transmittance, the haze (the initial haze), the light fastness, moist heat resistance, and the haze after the moist heat resistance test of the obtained laminate were evaluated by the following methods. The results are shown in Table 1.

1. Transmittance

The obtained laminate of the glass plate and the ultraviolet absorbing film was used as a measurement target, and the transmittance of an ultraviolet absorbing film containing the specific ultraviolet absorbing agent at 380 nm was measured using a UV/vis spectrometer (a UV/vis spectrometer UV3400 manufactured by Shimadzu Corporation).

Since the haze of the glass plate which is a base material, which is measured by a haze meter, was 0.20%, and the absorbance of the ultraviolet ray of 380 nm of the glass plate was 1% or less, the transmittance result obtained by measuring the laminate was used to evaluate the transmittance of the ultraviolet absorbing film of the present disclosure.

2. Haze (Initial Haze)

The haze was measured with a haze meter (manufactured by NIPPON DENSHOKU INDUSTRIES Co., Ltd., NDH4000) using the obtained laminate of the glass plate and the ultraviolet absorbing film. The haze of the ultraviolet absorbing film shown in Table 1 below is a measured value compensated based on the haze (0.20%) of the above-described glass plate itself.

3. Light Fastness

First, the transmittance of the obtained laminate of the glass plate and the ultraviolet absorbing film at a wavelength of 380 nm was measured using a spectrophotometer (model number: UV 3150) manufactured by Shimadzu Corporation.

Next, using a super-accelerated weather fastness tester [product name: EYE SUPER UV Tester, IWASAKI ELECTRIC Co., Ltd.], the obtained laminate of the glass plate and the ultraviolet absorbing film was irradiated with light (about 290 nm or less) of a metal halide lamp for 60 hours under the conditions of an illuminance of 90 mW/cm$^2$ (exposure energy: 90 mJ/cm$^2$), a temperature of 63° C., and a relative humidity of 50%.

After light irradiation, the transmittance of the obtained laminate of the glass plate and the ultraviolet absorbing film at a wavelength of 380 nm was measured in the same manner as described above using a spectrophotometer (model number: UV 3150) manufactured by Shimadzu Corporation.

The width of change in transmittance at a wavelength of 380 nm before and after the light irradiation was calculated, and the light fastness was evaluated as "particularly good" in a case where the width of change was less than 5%, the light fastness was evaluated as "good" in a case where the width of change was 5% or more and less than 10%, and the light fastness was evaluated as "bad" in a case where the width of change was 10% or more.

4. Moist Heat Resistance

The moist heat test was carried out with a constant temperature and humidity device (IG420, manufactured by Yamato Scientific Co., Ltd.) under the conditions of a temperature of 60° C. and a humidity of 90% RH. The transmittance at 380 nm after the lapse of 160 hours was measured by the above method. The width of change in transmittance at a wavelength of 380 nm before and after the moist heat resistance test was calculated, and the moist heat resistance was evaluated as "particularly good" in a case where the width of change was less than 5%, the moist heat resistance was evaluated as "good" in a case where the width of change was 5% or more and less than 10%, and the moist heat resistance was evaluated as "bad" in a case where the width of change was 10% or more.

The haze after the moist heat resistance test was measured by the same method as in (2. Initial haze) described above. The results are shown together in Table 1.

5. Yellowishness

The prepared and obtained laminate of the glass plate and the ultraviolet absorbing film was placed on white paper. One evaluation monitoring staff was asked to visually observe the laminate on the paper and evaluate whether or not the laminate had yellowishness.

Example 2 to Example 5

Ultraviolet absorbing compositions of Examples 2 to Example 5 were obtained in the same manner as in Example 1 except that the kind of the specific ultraviolet absorbing agent (the compound M-3) in Example 1 was changed to the kind shown in Table 1 below.

The same evaluation as in Example 1 was carried out using the obtained ultraviolet absorbing composition. The evaluation results are shown in Table 1 below.

Comparative Example 1 to Comparative Example 5

Ultraviolet absorbing compositions of Comparative Example 1 to Comparative Example 5 were obtained in the same manner as in Example 1 except that the kind of the specific ultraviolet absorbing agent (the compound M-3) in Example 1 was changed to comparative ultraviolet absorbing agents (a comparative compound H-1 to a comparative compound H-5) shown in Table 1 below.

The same evaluation as in Example 1 was carried out using the obtained composition. The evaluation results are shown in Table 1 below.

The structures of the comparative ultraviolet absorbing agents (the comparative compound H-1 to the comparative compound H-5) used in Comparative Examples are shown below.

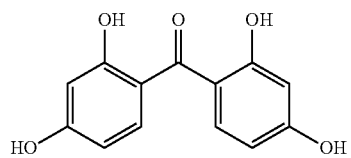

H-1

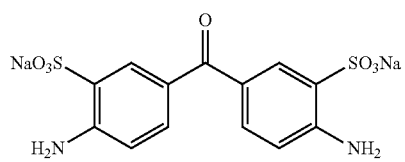

H-2

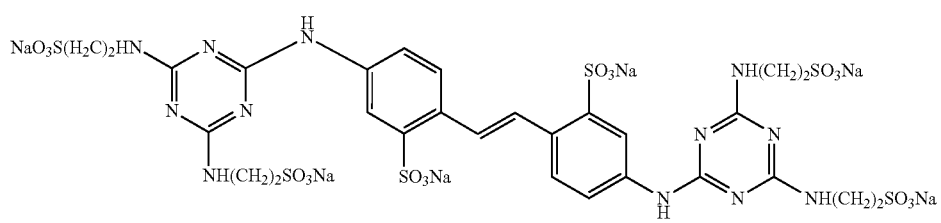

H-3

-continued

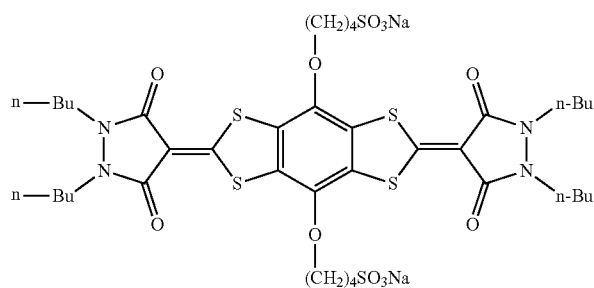

H-4

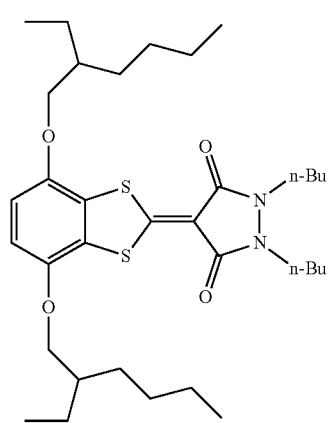

H-5

Example 6

2.0 parts by mass of the compound M-3, 98.0 parts by mass of polyvinyl alcohol, and 1,000 parts by mass of water were mixed, stirred at 40° C. for 1 hour to completely dissolve the mixture, whereby an ultraviolet absorbing composition was obtained. After cooling the composition to room temperature (25° C.), the obtained composition was formed to a coating film on a glass plate by spin coating (1,000 rotations/minute (rpm), 10 seconds), followed by drying on a hot plate at 100° C. for 20 seconds to form an ultraviolet absorbing film which is a cured substance of the ultraviolet absorbing composition of Example 6.

Example 7 to Example 9

Ultraviolet absorbing compositions of Examples 7 to Example 9 were obtained in the same manner as in Example 1 except that the kind of the specific ultraviolet absorbing agent (the compound M-3) in Example 6 was changed to the kind shown in Table 1 below.

The same evaluation as in Example 1 was carried out using the obtained ultraviolet absorbing composition. The evaluation results are shown in Table 1 below.

TABLE 1

| | Specific ultraviolet absorbing agent or comparative ultraviolet absorbing agent | Water-soluble polymer | Evaluation result | | | | | |
|---|---|---|---|---|---|---|---|---|
| | | | Light transmittance at 380 nm (%) | Initial haze | Light fastness | Moist heat resistance | Haze after moist heating | Yellow-ishness |
| Example 1 | Compound M-3 | PVA | 0.11 | 0.22 | Particularly good | Particularly good | 0.24 | No |
| Example 2 | Compound M-5 | PVA | 0.15 | 0.23 | Particularly good | Particularly good | 0.28 | No |
| Example 3 | Compound M-8 | PVA | 0.2 | 0.21 | Particularly good | Good | 0.4 | No |
| Example 4 | Compound M-11 | PVA | 0.18 | 0.2 | Particularly good | Particularly good | 0.26 | No |
| Example 5 | Compound M-18 | PVA | 0.22 | 0.24 | Particularly good | Good | 0.42 | No |

TABLE 1-continued

| | Specific ultraviolet absorbing agent or comparative ultraviolet absorbing agent | Water-soluble polymer | Evaluation result | | | | | |
|---|---|---|---|---|---|---|---|---|
| | | | Light transmittance at 380 nm (%) | Initial haze | Light fastness | Moist heat resistance | Haze after moist heating | Yellowishness |
| Comparative Example 1 | Comparative Compound H-1 | PVA | 12 | 0.4 | Bad | Bad | 6.1 | No |
| Comparative Example 2 | Comparative Compound H-2 | PVA | 8.5 | 0.52 | Bad | Bad | 8.1 | Yes |
| Comparative Example 3 | Comparative Compound H-3 | PVA | 6.1 | 0.8 | Bad | Bad | 9.5 | No |
| Comparative Example 4 | Comparative Compound H-4 | PVA | 1.2 | 4.5 | Good | Bad | 18 | Yes |
| Comparative Example 5 | Comparative Compound H-5 | PVA | 48 | 14 | Bad | Bad | 68 | Yes |
| Example 6 | Compound M-3 | PVA | 6 | 0.1 | Particularly good | Particularly good | 0.1 | No |
| Example 7 | Compound M-8 | PVA | 8 | 0.1 | Particularly good | Particularly good | 0.3 | No |
| Example 8 | Compound M-11 | PVA | 4 | 0.1 | Particularly good | Particularly good | 0.1 | No |
| Example 9 | Compound M-18 | PVA | 7 | 0.1 | Particularly good | Particularly good | 0.2 | No |

From the results shown in Table 1, it has been seen that all of the laminates of Example 1 to Example 5, having the ultraviolet absorbing film which is a cured substance of the ultraviolet absorbing composition containing the specific ultraviolet absorbing agent of the present disclosure, have an excellent property of blocking an ultraviolet ray of 380 nm, a low initial haze, good light fastness, and good moist heat resistance. Further, not only the initial haze is good, but also the haze after the moist heat resistance test is not significantly increased, and thus the haze is at a level where there is no problem in practical use.

Further, in the laminates of Example 6 to Example 9 as well, which have a lower content of the specific ultraviolet absorbing agent, the property of blocking an ultraviolet ray of 380 nm, which is not problematic in practical use, is exhibited although the ultraviolet shielding property is slightly low as compared with Example 1 to Example 5. Further, the initial haze is low, and the light fastness and the moist heat resistance are good. In addition, the haze after the moist heat resistance test is not significantly increased, and thus the haze is at a level where there is no problem in practical use.

On the other hand, Comparative Examples 1 to 3 and Comparative Example 5, in which the comparative ultraviolet absorbing agent was used instead of the specific ultraviolet absorbing agent, are inferior in the property of blocking an ultraviolet ray of 380 nm. The laminate of Comparative Example 4 containing the comparative ultraviolet absorbing agent (H-4) having two benzothiolane skeletons in the molecule has a good initial haze; however, the haze is significantly increased after the moist heat resistance test due to the crystallization of the ultraviolet absorbing agent.

The present disclosure of JP2019-122032 filed on Jun. 28, 2019, is incorporated herein in its entirety by reference.

All documents, patent applications, and technical standards described in the present disclosure are incorporated in the present disclosure by reference, to the same extent as in the case where each of the documents, patent applications, and technical standards is specifically and individually described.

What is claimed is:

1. An ultraviolet absorbing agent represented by General Formula (2),

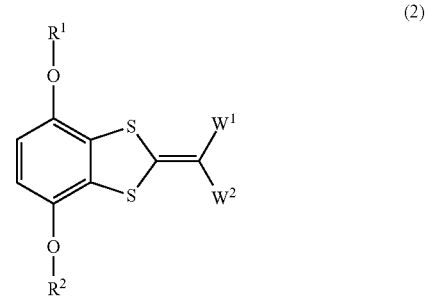

wherein, in General Formula (2), $R^1$ and $R^2$ each independently represent a monovalent substituent, $W^1$ and $W^2$ each independently represent a hydrogen atom, a cyano group, a carbamoyl group, a sulfamoyl group, a nitro group, an acyl group, an alkylsulfonyl group, an arylsulfonyl group, an alkylsulfinyl group, an arylsulfinyl group, an alkoxycarbonyl group, an aryloxycarbonyl group, an alkyl group, an aryl group, or a heterocyclic group, where at least one of $W^1$ or $W^2$ represents a substituent having a Hammett's substituent constant σp value of 0.2 or more, and $W^1$ and $W^2$ may be bonded to each other to form a ring, and at least one group of $R^1$, $R^2$, $W^1$, or $W^2$ has an acid group selected from the group consisting of a phosphoric acid group and a sulfonic acid group represented by $SO_3X$, wherein X represents a hydrogen atom or a countercation of $-SO_3^-$.

2. The ultraviolet absorbing agent according to claim 1, wherein the acid group is the sulfonic acid group.

3. The ultraviolet absorbing agent according to claim 1, wherein a solubility in water at 25° C. is 1% by mass or more.

4. An ultraviolet absorbing composition comprising:
the ultraviolet absorbing agent according to claim 1; and
an aqueous medium.

5. The ultraviolet absorbing composition according to claim 4, further comprising:
a water-soluble polymer.

6. An ultraviolet absorbing film,
wherein the ultraviolet absorbing film comprises the ultraviolet absorbing agent according to claim 1.

7. A laminate comprising:
a base material; and
the ultraviolet absorbing film according to claim 6, formed on the base material.

8. An ultraviolet absorbing agent represented by General Formula (3),

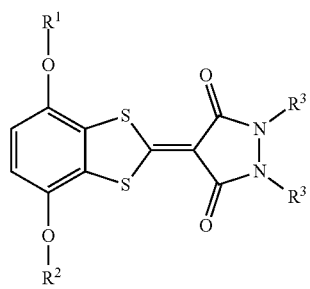

wherein, in General Formula (3), $R^1$ and $R^2$ each independently represent a monovalent substituent,
$R^3$ represents an alkyl group, an aryl group, or a heterocyclic group, and
at least one group of $R^1$, $R^2$, or $R^3$ has an acid group selected from the group consisting of a phosphoric acid group and a sulfonic acid group represented by $SO_3X$, wherein X represents a hydrogen atom or a countercation of $—SO_3^-$.

9. The ultraviolet absorbing agent according to claim 8, wherein the acid group is the sulfonic acid group.

10. The ultraviolet absorbing agent according to claim 8, wherein a solubility in water at 25° C. is 1% by mass or more.

11. An ultraviolet absorbing composition comprising:
the ultraviolet absorbing agent according to claim 8; and
an aqueous medium.

12. The ultraviolet absorbing composition according to claim 11, further comprising:
a water-soluble polymer.

13. An ultraviolet absorbing film,
wherein the ultraviolet absorbing film comprises the ultraviolet absorbing agent according to claim 8.

14. A laminate comprising:
a base material; and
the ultraviolet absorbing film according to claim 13, formed on the base material.

15. A compound represented by General Formula (4),

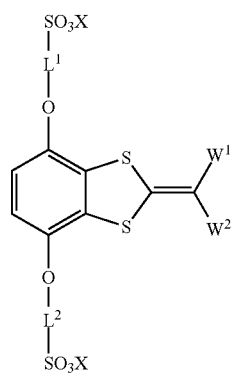

wherein, in General Formula (4), $L^1$ and $L^2$ each independently represent an alkylene group,
X's each independently represent a hydrogen atom or a countercation of $–SO_3^-$, and
$W^1$ and $W^2$ each independently represent a hydrogen atom, a cyano group, a carbamoyl group, a sulfamoyl group, a nitro group, an acyl group, an alkylsulfonyl group, an arylsulfonyl group, an alkylsulfinyl group, an arylsulfinyl group, an alkoxycarbonyl group, an aryloxycarbonyl group, an alkyl group, an aryl group, or a heterocyclic group, where at least one of $W^1$ or $W^2$ represents a substituent having a Hammett's substituent constant σp value of 0.2 or more, and $W^1$ and $W^2$ may be bonded to each other to form a ring.

* * * * *